US006136320A

United States Patent [19]

Arntzen et al.

[11] Patent Number: 6,136,320

[45] Date of Patent: *Oct. 24, 2000

[54] VACCINES EXPRESSED IN PLANTS

[75] Inventors: Charles Joel Arntzen; Dominic Man-Kit Lam, both of The Woodlands, Tex.

[73] Assignee: Prodigene, Inc., College Station, Tex.

[ * ] Notice: This patent is subject to a terminal disclaimer.

[21] Appl. No.: 09/111,330

[22] Filed: Jul. 7, 1998

Related U.S. Application Data

[60] Continuation of application No. 08/479,742, Jun. 7, 1995, Pat. No. 5,914,123, which is a division of application No. 08/026,393, Mar. 4, 1993, Pat. No. 5,612,487, and a continuation-in-part of application No. PCT/US94/02332, Mar. 4, 1994, which is a continuation-in-part of application No. 08/026,393, which is a continuation-in-part of application No. 07/750,049, Aug. 26, 1991, abandoned, which is a continuation-in-part of application No. 08/156,508, Nov. 23, 1993, Pat. No. 5,484,719.

[51] Int. Cl.$^7$ .................................................... A61K 39/12

[52] U.S. Cl. .................................... 424/204.1; 424/225.1; 424/227.1; 424/223.1; 424/195.1

[58] Field of Search ............................ 424/225.1, 227.1, 424/93.2, 195.1, 204.1, 223.1; 800/298, 288

[56] References Cited

U.S. PATENT DOCUMENTS

| | | | |
|---|---|---|---|
| 4,428,941 | 1/1984 | Galibert et al. . | |
| 4,803,164 | 2/1989 | Hitzeman et al. | 435/69.3 |
| 4,920,209 | 4/1990 | Davis et al. . | |
| 4,940,835 | 7/1990 | Shah et al. . | |
| 4,956,282 | 9/1990 | Goodman et al. . | |
| 5,024,938 | 6/1991 | Nozaki et al. | 435/69.3 |
| 5,316,931 | 5/1994 | Donson et al. . | |
| 5,324,646 | 6/1994 | Buising et al. . | |
| 5,484,719 | 1/1996 | Lam et al. . | |
| 5,654,184 | 8/1997 | Curtiss . | |
| 5,679,880 | 10/1997 | Curtiss . | |
| 5,686,079 | 11/1997 | Curtiss . | |

FOREIGN PATENT DOCUMENTS

| | | | |
|---|---|---|---|
| 0 235 391A | 9/1987 | European Pat. Off. | C07K 13/00 |
| 0 278 541 | 1/1988 | European Pat. Off. . | |
| 0 510 773 A1 | 4/1992 | European Pat. Off. | C12N 15/50 |
| WO 87/00865 | 2/1987 | WIPO | C12P 21/00 |
| WO 89 01514 | 2/1989 | WIPO | C12N 15/00 |
| WO 90/02484 | 3/1990 | WIPO | A01H 5/00 |
| WO 90/10076 | 9/1990 | WIPO | C12N 15/82 |
| WO 92 18618 | 10/1992 | WIPO | C12N 7/01 |
| WO 93/23421 | 11/1993 | WIPO | C07K 3/00 |
| WO 94/20135 | 9/1994 | WIPO | A61K 39/00 |
| WO 95/21248 | 8/1995 | WIPO | C12N 15/00 |
| WO 96/02649 | 2/1996 | WIPO | C12N 15/40 |
| WO 96/12801 | 5/1996 | WIPO | C12N 15/00 |

OTHER PUBLICATIONS

Aizpurua, H.J., de, Russell–Jones, G.J., "Oral Vaccination Identification of Classes of Proteins that Provoke an Immune Response upon Oral Feeding," *J. Exp. Med.*, vol. 167., pp. 440–451 (1988).

An, G., "Binary Ti Vectors for Plant Transformation and Promoter Analysis", *Methods in Enzymology*, vol. 153, pp. 292–305, (1987).

Arntzen, Charles et al., "Production of Candidate Oral Vaccines in Edible Tissues of Transgenic Plants", *Vaccines*, 94:229–344 (1994).

Benfey, P.N., Chua, N.H., "Regulated Genes in Transgenic Plants", *Science*, vol. 244, pp. 174–181 (1989).

Bidney, D. et al., "Microprojectile bombardment of plant tissues increases transformation frequency by *Agrobacterium tumefaciens", Plant Molecular Biology*, 18:301–313 (1992).

Blair, J.G., "Test–Tube Gardens", *Science*, vol. 82, pp. 71–73 (1982).

Bovsun, M., "Tobacco Produces Hepatitis Antigens: Vaccines To Go Into Bananas Next", *Biotechnology Newswatch via NewsNet*, 12(24), Dec. 21, 1992).

Brisson, N., "Plant Virus Vectors: Cauliflower Mosaic Virus", *Methods in Enzymology*, vol. 118, Academic Press, Inc., pp. 659–668 (1986).

Capron, A., et al., "Immunity to Schistosomes: Progress Toward Vaccine", *Science*, vol. 238, pp. 1065–1072 (1987).

Cattaneo, R., "Signals regulating hepatitis B surface antigen transcription", *Nature* 305:336–338 (Sep. 1983).

Chang, A. et al., "Characterization of a genetically reconstituted high–affinity system for serotonin transport", *Proc. Natl. Acad. Sci. USA*, vol. 86, pp. 9611–9615 (1989).

Christou, P., et al., "Soybean genetic engineering—commercial production of transgenic plants", *Trends Biotechnol.*, vol. 8, pp. 145–151 (1990).

Clontech Laboratories, Inc., Palo Alto, California, Product Catalog, p. 18.4, (1991).

Coghlan, A., "When beans means vaccines", *New Scientist*, 135:1829:19, Jul. 1992.

Daie, J. et al., "Plants Factories: Production of Industrial Proteins and Non–Food Products in Transgenic Plants", *Agro Food Industry Hi–Tech*, 4(1):6–8 (Jan./Feb. 1993).

Datta, S.K., et al., "Genetically Engineered Fertile Midica–Rice Recovered From Protoplasts", *Bio/Technology*, vol. 8, pp. 736–740 (1990).

(List continued on next page.)

*Primary Examiner*—Mary Mosher
*Attorney, Agent, or Firm*—Patricia A. Sweeney; Zarley, McKee, Thomte, Voorhees & Sease

[57] ABSTRACT

The anti-viral vaccine of the present invention is produced in transgenic plants and then administered through standard vaccine introduction method or through the consumption of the edible portion of those plants. A DNA sequence encoding for the expression of a surface antigen of a viral pathogen is isolated and ligated to a promoter which can regulate the production of the surface antigen in a transgenic plant. This gene is then transferred to plant cells using a procedure that results in its integration into the plant genome, such as through the use of an *Agrobacterium tumenfaciens* plasmid vector system. Preferably, the foreign gene is expressed in an portion of the plant that is edible by humans or animals. In a preferred procedure, the vaccine is administered through the consumption of the edible plant as food, preferably in the form of a fruit or vegetable juice which can be taken orally.

10 Claims, 11 Drawing Sheets

OTHER PUBLICATIONS

Declaration Under 37 CFR § 1.131 of Charles J. Arntzen Jan. 10, 1996.
Deak, M., et al., "Transformation of Medicago by Agrobacterium Mediated Gene Transfer", *Plant Cell Reports*, vol. 5, pp. 97–100 (1986).
dePalma, A., "Agricultural Genetics Co., Ltd. Produces Vaccines for Animals in Cowpea Plants" *Genetic Engineering News*, 12(13):1, 15 (Sep. 24, 1997.1, 1992).
DeWet, J.M.J. et al., "Exogenous gene transfer in maize (*Zea mays*) using DNA–treated pollen", *Experimental Manipulation of Ovule Tissue*, G.P. Chapman et al. ed., Longman, New York–London, p. 197–209 (1985).
Dickinson, B.L. et al., "Dissociation of *Escherichia coli* Heat–Labile Enterotoxin Adjuvanticity from ADP–Robosyltransferase Activity", *Infection and Immunity*, vol. 63, No. 5, pp. 1617–1623.
Dittman, R.E., "Eradicating Disease: Trends in Vaccine Development", *Summer 1993 Priorites*, pp. 40–42.
Elliston, K. and Messing J., "The Molecular Architecture of Plant Genes and Their Regulation", *Plant Biotechnology*, Kung/Arntzen, ed., pp. 115–139 (1989).
Fields, et al., "Virology", Raven Press, N.Y., pp. 1160–1161 and 1219–1221.
Fitchen, J., "Production of Monoclonal Antibodies and Candidate Vaccines in Plants and Plant Cell Cullures", (Abstract) From Meeting of the Tissue Culture Association on Regulation of Cell and Tissue Differentiation, Research Triangle Park, North Carolina USA (Jun. 4–7, 1994).
Forrest, B.D., "Women, HIV, and Mucosal Immunity", *The Lacet*, vol. 337, pp. 835–836 (1991).
Fraley, R.T., "Genetic Engineering for Crop Improvement", *Plant Biotechnology*, Kung/Arntzen, ed., pp. 395–407 (1989).
Frasch, A.C.C. et al., "Comparison of Genes Encoding *Trypanosoma cruzi* Antigens", *Parasitology Today*, vol. 7(6), pp. 148–151 (1991).
Fromm, M., et al., "Expression of genes transferred into monocot and dicot plant cells by electroporation", *Proc. Natl. Acad. Sci. USA*, vol. 82, pp. 5824–5828 (1985).
Fromm, M.E., et al., "Inheritance and Expression of Chimeric Genes in the Progeny of Transgenic Maize Plants", *Bio/Technology*, vol. 8, pp. 833–839 (1990).
Fu, Z.F. et al, "Oral vaccination of raccoons (*Procyon lotor*) with baculovirus–expressed rabies virus glycoprotein", *Vaccine*, 11(9):925–928 (1993).
Fütterer, J., et al., "Cauliflower mosaic virus as a gene expression vector for plants", *Physiol. Plant*, vol. 79, pp. 154–157, Copenhagen 1990.
Ganem, D. et al., "The Molecular Biology of the Hepatitis B Viruses", *Ann. Rev. Biochem*, 56:651–693 (1987).
Gatenby, A.A., "Regulation and Expression of Plant Genes in Microorganisms", *Plant Biotechnology*, pp. 93–112, Kung/Arntzen ed., (1989).
Glass, R.I. et al., "Nucleotide Sequence of the Structural Glycoprotein VP7 Gene of Nebraska Calf Diarrhea Virus Rotavirus: Comparison with Homologous Genes from Four Strains of Human and Animal Rotaviruses", *Virology*, 141:292–298 (1985).
Godet, M., et al., "Processing and Antigenicity of Entire and Anchor–Free Spike Glycoprotein S of Coronavirus TGEV Expressed by Recombinant Baculovirus," *Virology*, vol. 185, pp. 732–740 (1991).
Gordon–Kamm, W.J., et al., "Transformation of Maize Cells and Regeneration of Fertile Transgenic Plants", *The Plant Cell* 2:603–618 (Jul. 1990).
Haq, T.A. , et al., "Oral Immunization with a Recombinant Bacterial Antigen Produced in Transgenic Plants", *Science* 268:714–716 (May 5, 1995) XP002024034).
Hess, D., "Pollen–Based Techniques in Genetic Manipulation", *Review of Cytology*, vol. 107, pp. 367–395 (1987).
Hinchee, M.A.W., et al., "Production of Transgenic Soybean Plants Using Agrobacterium–Mediated DNA Transfer", *Bio/Technology*, vol. 6, pp. 915–922 (1988).
Hoffman, L., et al., "A Modified Storage Protein in Synthesized, Processed, and Degraded in the Seeds of Transgenic Plants," *Plant Molecular Biology*, vol. 11, pp. 717–729 (1988).
Hoffman, L., et al., "Progress Toward Malaria Preerythrocytic Vaccines", *Science*, vol. 252, pp. 520–521 (1991).
Horsch, R.B., et al., "Leaf Disc Transformation", *Plant Molecular Biology Manual* A5:1–9 (1988).
Jacobs, L. et al., The nucleotide sequence of the peplomer gene of porcine transmissible gastroenteritis virus (TGEV): comparison with the sequence of the peplomer protein of feline infectious peritonitis virus (FIPv):, *Virus Research* 8:363–371 (1987).
Kaslow, D.C., et al., "Induction of *Plasmodium falciparum* Transmission–Blocking Antibodies by Recombinant Vaccinia Virus", *Science*, 252, pp. 1310–1313 (1991).
Khusmith, S., et al., "Protection Against Malaria by Vaccination with Sporozoite Surface Protein 2 Plus CS Protein", *Science*, 252, pp. 715–718 (1991).
Klee, H., et al., "Agrobacterium–Mediated Plant Transformation and its Further Applications to Plant Biology", *Ann. Rev. Plant Physiol.*, 1987, 38:467–486.
Klee, H.J., et al., "Transfrmation of Plants by *Agrobacterium Tumefaciens", Cell Culture and Somatic Cell Genetics of Plants*, vol. 6, Molecular Biology of Plant Nuclear Genes, pp. 2–25 (1989).
Klein, T.M. et al., "Factors Influencing Gene Delivery into *Zea Mays* Cells by High–Velocity Microprojectiles", *Bio/Technology*, vol. 6, pp. 559–563 (1988).
Klein, T.M., et al., "Applications of the Particle Gun in Plant Biology", *Progress in Plant Cellular and Molecular Biology*, pp. 56–66.
Kovgan, A.A. Chemical Abstracts, 110:207163 (Abstract No. 207160n) "Potential Vector for Introducing Animal Virus Genes into Cells of Higher Plants", abstract of an article in *Bioteknnologiya* 5:148–54 (1989).
Kupper, Hans, et al, "Cloning of cDNA of major antigen of foot and mouth disease virus and expression in *E. coli", Nature* 289:550–559 (1981).
Kuriyana, S., et al., "Enhancing of Oral Adjuvants on Anti–HBs Responses Induced by Hepatitis B Vaccine", *Clin. Exp. Immunol.*, 72:383–389 (1988) (abstract).
Lanar, D., et al., "Identification of Paramyosin as Schistosome Antigen Recognized by Intradermally Vaccinated Mice", *Science*, 234:593–596 (1986).
Larkins, B., et al., "Transcriptional Regulation of Maize Zein Gene", (Abstract), *J. Cell. Biochem. Suppl. 0* (9 part C), p. 264 (1985).
Laude, H., et al., "Molecular biology of transmissible gastroenteritis virus", *Veterinary Microbiology* 23:147–154 (1990).
Liew, F.Y., ed., *Vaccination Strategies of Tropical Diseases* (1989) table of contents only.

Lubeck, M.D., "Immunogenicity and Efficacy Testing in Chimpanzees of an Oral Hepatitis B Vaccine Based on Live Recombinant Adenovirus", *Proc. Natl. Acad. Sci. USA*, 86:6763–6737 (1989) (abstract).

Mackow, E. et al., "Immunization with Baculovirus–Expressed VP4 Protein Passively Protects against Simian and Murine Rotavirus Challenge", *J. of Virology* 64(4):1698–1703 (Apr. 1990).

Mackow, E. et al., "The Rhesus Rotavirus Outer Capsid Protein VP4 Functions as a Hemagglutinin and is Antigenically Conserved When Expressed by a Baculovirus Recombinant", *J. Virology*, 64(4) 1661–1668 (Apr. 1989).

Maloney, M.M. et al., "High efficiency transformation of *Brassica napus* using Agrobacterium vectors", *Plant Cell Reports* 8:238–242 (1989).

Maniatis, T., et al., *Molecular Cloning, A Laboratory Manual*, Cold Spring Harbor (1982), p. 368–369.

Maskell, D., et al., "Attenuated *Salmonella typhimurium* as Live Oral Vaccines and Carriers for Delivering Antigens to the Secretory Immune System", *Vaccines* 86, Cold Spring Harbor Lab, N.Y., pp. 215–217 (1986).

Mason, H.S., et al., "Expression of Candidate Oral Vaccine Antigens in Transgenic Plants", *Journal of Cellular Biochemistry Supplement*, 18a:98 (1994).

Mason, H.S. et al., "Expression of Hepatitis B Surface Antigen in Transgenic Plants", *Proc. Natl. Acad. Sci. USA*, vol. 89, pp. 11745–11749 (1992).

Mason, H. et al., "Transgenic plants as vaccine production systems", *Trents in Biotechnology*, 13(9):388–392 (Sep. 1995) (XP001013024).

Mason, H. et al., "Immunogenicity of Candidate Vaccine Antigens Produced in Transgenic Plants", (Abstract) 4th International Congress of Plant Molecular Biology (Jun. 1994).

McAdam, K.P.W.J., *New Strategies in Parasitology* (1989), table of contents only.

McCabe, D.E., et al., "Stable Transformation of Soybean (Glycine Max) by Particle Acceleleration", *Bio/Technology* 6:923–926 (1988).

McCormick, S. et al., "Leaf disc transformation of cultivated tomato (*L. esculentum*) using *Agrobacterium tumefaciens", Plant Cell Reports* 5:81–84 (1986).

Melnick, J.L., "Virus Vaccines: Principles and Prospects", *Bulletin of the World Health Organization*, 67(2):105–112 (1989).

Mitchell, G.F., "Glutathione S–transferases–Potential Components of Anti–schistosome Vaccines?", *Parasitology Today* 5:34–37 (1989).

Miyanohara, et al., "Expression of Hepatitis B Surface Antigen Gene in Yeast", *Proc. Nat'l Acad. Sci. USA* 80:105 (1983).

Moffat, A.S. "Genetically Engineered Plants Point Toward Edible Vaccines", *Genetic Engineering News*, L3(12):1, 19 (Jun. 15, 1993).

Moffat, A.S., "Exploring Transgenic Plants as a New Vaccine Source", *Science* 268:658–660 (1995).

Murray, P.K., "Molecular vaccines against animal parasites", *Vaccines*, 7:291–299 (1989).

Neuhaus, G., et al., "Transgenic rapeseed plants obtained by the microinjection of DNA into microspore–derived embryoids", *Theor. Appl. Genet.* 75:30–36 (1987).

Neuhaus, G., et al., "Plant transformation by microinjection techniques", *Physiologia Plantarum*, 79:213–217, Copenhagen (1990).

Ohta, Yasuo, "High–efficiency genetic transformation of maize by a mixture of pollen and exogenous DNA", *Proc. Nat'l. Acad. Sci. USA*, 83:715–719 (1986).

Ohtani, T., et al., "Normal and Lysine–Containing Zeins are Unstable in Transgenic Tobacco Seeds", *Plant Molecular Biology*, 16:117–128 (1991).

Pasek, M., et al., "Hepatitis B virus genes and their expression in *E. coli", Nature*, 282:575–579 (1979).

Paszkowski, J., et al., "Cell Culture and Somatic Cell Genetics of Plants", vol. 6, *Molecular Biology of Plant Nuclear Genes* pp. 52–68 (1989).

Paul, P.S. et al, "Immunogens for rotaviruses", *Veterinary Microbiology*, 37:299–317 (1993).

Peng, Y.W., et al., "Organization and development of horizontal cells in the goldfish retina, I: The use of monoclonal antibody AT101", *Visual Neuroscience*, 6:357–370 (1991).

Persing, D.H., et al., :A frameshift mutation in the pre–S region of the human hepatitis B virus genome allows production of surface antigen particles but eliminates binding to polymerized albumin, *Proc. Nat'l. Acad. Sci. USA* 82:3440–3444 (1985).

Porta, C. et al., "Cowpea Mosaic Virus as an Efficient Epitope Presentation System", (Abstract) 4th International Congress of Plant Molecular Biology (Jun. 1994).

Porta, C. et al., Development of Cowpea Mosaic Virus as a High–Yielding System for the Presentation of Foreign Peptides{, *Virology* 202:949–955 (Aug. 1994) (XP002024036).

Potrykus, I., "Gene Transfer to Plants: Assessment of Published Approaches and Results", *Annu. Rev. Plant Physiol., Plant Mol. Biol.* 42:205–225 (1991).

Raineri, D.M., et al., Agrobacterium–Mediated Transformation of Rice (*Oryza Sativa* L.), *Bio/Technology* 8:33–38 (1990).

Rassachaert, D. et al., "The Predicted Primary Structure of the Peplomer Protein E2 of the Porcine Coronavirus Transmissible Gastroenteritis Virus", *J. Gen. Virol.* 68:1883–1890 (1987).

Rhodes, C.A., et al., "Genetically Transformed Maize Plants from Protoplasts", *Science*, 240:204–207 (1989).

Richman, L.K., et al., "Enterically Induced Immunologic Tolerance, I. Induction of Suppressor T Lymphocytes by Intragastric Administration of Soluble Proteins", *J. Immunol.*, 121:2429–2434 (1978).

Rocha–Sosa, et al., "Both Developmental and Metabolic Signals Activate the Promoter of a Class 1 Patatin Gene", *The EMBO Journal*, 8(1):23–29 (1989).

Saif, L.J., "Coronavirus immunogens", *Veterinary Microbiology*, 37:285–297 (1993) (XP002024044).

Salfeld, J., et al., "Antigenic Determinants and Functional Domains in Core Antigen and e Antigen from Hepatitis B Virus", *J. Virology*, 63(2):798–808 (1989).

Sanchez, C.M., et al., "Genetic Evolution and Tropism of Transmissible Gastroenteritis Coronaviruses", *Virology*, 190:92–105 (1992).

Sanford, J.C., "Biolistic Plant Transformation", *Physiol. Plant*. 79:206–209 (1990).

Schodel, F., et al., "Recombinant HBV Core Particles Carrying Immunodominant B–Cell Epitopes of HBV Pre–S2 Region", *Vaccines 90*, published by Cold Spring Harbor Laboratory Press (Cold Spring Harbor, NY), F. Brown, et al., eds. pp. 293–198 (1990).

Schodel, F., et al., "Expression of Hepatitis B Virus Antigens in Attentuated Salmonellae for Oral Immunization", *Res. Microbiol.*, 141:831–837 (1990) (abstract).

Schodel, F., et al., "Expression of Hepatitis B Virus Core T–cell Epitopes and pre–S2 B–cell Epitope as Fusion Protein with LT–B in Salmonella for Oral Vaccine", *Progress in Hepatitis B Immunization*, published by Colloque INSERM/ John Libbey Eurotext Ltd., Coursaget, P., et al., eds., 43–50 (1990).

Service, R.F., "Triggering the First Line of Defense", *Science* 265:1522–1524 (1995).

Shanin, E.A., "Gene Transfer System for Potato", *Hort. Science*, 21:1199–1201 (1986).

Shimamoto, K. et al., "Fertile transgenic rice plants regenerated from transformed protoplasts", *Nature* 338:274–276 (1989).

Thanavala, Y., et al., "Immunogenicity of transgenic plant–derived hepatitis B surface antigen", *Proc. Natl. Acad. Sci. USA*, 92:3358–3361 (Aprip 1995) XP002024002).

Toriyami, K. et al., "Transgenic rice plants after direct gene transfer into protoplasts", *Bio/Technology* 6:1072–1074 (1988).

Touchette, N., "AIDS Research and Mucosal Immune Studies Begin to Gel", *The Journal of NIH Research*, 3:65–70 (1991).

Umbeck, P. et al., "Genetically Transformed Cotton (*Gossypium Hirsutum* L.) Plants", *Bio/Technology* 5:263–266 (1987).

Usha, R. et al., "Expression of an Animal Virus Antigenic Site on the Surface of a Plant Virus Particle", *Virology*, 197:366–374 (1993).

Valenzuela, P. et al., "Synthesis and assembly of hepatitis B virus surface antigen particles in yeast", *Nature* 298:347–350 (1982).

Vaughn, E. et al., "Sequence Comparison of Porcine Respiratory Coronavirus Isolates Reveals Heterogeneity in the S, 3, and 3–1 Genes", *J. Virology* 69:3176–3184 (May 1995).

Watson, J.D., *Recombinant DNA: A Short Course*, Cold Spring Harbor Laboratory, Chapter 13, pp. 164–175.

Weber, J.L., "*Plasmodium berghei*: Cloning of the Circumsporozoite Protein Gene", *Exp. ParasitologyExp. Parasitology*, 63:295–300 (1987).

Weising, K. et al., Foreign Genes in Plants: Transfer, Structure, Expression, and Applications, *Annu. Rev. Genet.*, 22:421–477 (1988).

Wenzler, H.C., et al., "Analysis of a chimeric class–I patatin– GUS gene in transgenic potato plants: High–level expression in tubers and sucrose–inducible expression in cultured leaf and stem explants", *Plant Mol. Biol.* 12:41–50 (1989).

White, F.F., Chapter 1, "Vectors for Gene Transfer in Higher Plants", *Plant Biotechnology*, pp. 3–34 (1989).

Wu, R., Chapter 2, "Methods for Transforming Plant Cells", *Plant Biotechnology*, 35–51 (1989).

Zhen, Fang Fu et al., "Oral vaccination of racoons (*Procyn lotor*) with baculovirus–expressed rabies virus glycoprotein", *Vaccine.*, vol. 11, Issue 9 (1993).

Zhang, H.M. et al., "Transgenic rice plants produced by electroporation–mediated plasmid uptake into protoplasts", *Plant Cell Rep.*, 7:379–384 (1988).

Zhang, W., et al., "Efficient regeneration of transgenic plants from rice protoplasts and correctly regulated expression of the foreign gene in the plants", *Theor. Appl. Genet.*, 76:835–840 (1988).

Zhang, S. et al., "Boosted Mucosal Immune Responsiveness in the Intestine by Actively Transported Hexose", *Gastroenterol.*, vol. 103, pp. 1162–1166 (1992).

RB = RIGHT T-DNA BORDER
LB = LEFT T-DNA BORDER
GUS = β -GLUCURONIDASE GENE
S = HBsAg GENE
Nt = NOPALINE SYNTHASE TERMINATOR
Np = NOPALINE SYNTHASE PROMOTER
NPT = NEOMYCIN PHOSPHOTRANSFERASE II GENE
35p = CUALIFLOWER MOSAIC VIRUS 35S PROMOTER
35d = 35S PROMOTER WITH DUPLICATED ENHANCER

RB = RIGHT T-DNA BORDER
LB = LEFT T-DNA BORDER
GUS = β -GLUCURONIDASE GENE
S = HBsAg GENE
Nt = NOPALINE SYNTHASE TERMINATOR
Np = NOPALINE SYNTHASE PROMOTER
NPT = NEOMYCIN PHOSPHOTRANSFERASE II GENE
35p = CUALIFLOWER MOSAIC VIRUS 35S PROMOTER
35d = 35S PROMOTER WITH DUPLICATED ENHANCER
TL = TOBACCO ETCH VIRUS 5' NONTRANSLATED LEADER

VACCINES EXPRESSED IN PLANTS

RELATED APPLICATIONS

This is a continuation of U.S. Ser. No. 08/479,742 filed Jun. 7, 1995, U.S. Pat. No. 5,914,123, which is a divisional of U.S. Ser. No. 08/026,393 filed Mar. 4, 1993, which issued as U.S. Pat. No. 5,612,487 Mar. 18, 1997, and a continuation-in-part of copending PCT application Ser. No. PCT/US94/02332 filed Mar. 4, 1994 (designating the US) which is a continuation-in-part of copending application Ser. No. 08/026,393 filed Mar. 4, 1993, which itself is a continuation-in-part of Ser. No. 07/750,049 filed Aug. 26, 1991 (now abandoned). This application is also a continuation-in-part of application Ser. No. 08/156,508 filed Nov. 23, 1993, which issued as U.S. Pat. No. 5,484,719 Jan. 16, 1996.

BACKGROUND OF THE INVENTION

This invention relates generally to vaccines and more particularly to the production of oral vaccines in edible transgenic plants and the administration of the oral vaccines such as through the consumption of the edible transgenic plants by humans and animals.

Diseases have been a plague on civilization for thousands of years, affecting not only man but animals. In economically advanced countries of the world, diseases are 1) temporarily disabling; 2) permanently disabling or crippling; or 3) fatal. In the lesser developed countries, diseases tend to fall into the latter two categories, permanently disabling or crippling and fatal, due to many factors, including a lack of preventative immunization and curative medicine.

Vaccines are administered to humans and animals to induce their immune systems to produce antibodies against viruses, bacteria, and other types of pathogenic organisms. In the economically advanced countries of the world, vaccines have brought many diseases under control. In particular, many viral diseases are now prevented due to the development of immunization programs. The virtual disappearance of smallpox, certainly, is an example of the effectiveness of a vaccine worldwide. But many vaccines for such diseases as poliomyelitis, measles, mumps, rabies, foot and mouth, and hepatitis B are still too expensive for the lesser developed countries to provide to their large human and animal populations. Lack of these preventative measures for animal populations can worsen the human condition by creating food shortages.

The lesser developed countries do not have the monetary funds to immunize their populations with currently available vaccines. There is not only the cost of producing the vaccine but the further cost of the professional administration of the vaccine. Also, some vaccines require multiple doses to maintain immunity. Therefore, often, the countries that need the vaccines the most can afford them the least.

Underlying the development of any vaccine is the ability to grow the disease causing agent in large quantities. At the present, vaccines are usually produced from killed or live attenuated pathogens. If the pathogen is a virus, large amounts of the virus must be grown in an animal host or cultured animal cells. If a live attenuated virus is utilized, it must be clearly proven to lack virulence while retaining the ability to establish infection and induce humoral and cellular immunity. If a killed virus is utilized, the vaccine must demonstrate the capacity of surviving antigens to induce immunization. Additionally, surface antigens, the major viral particles which induce immunity, may be isolated and administered to proffer immunity in lieu of utilizing live attenuated or killed viruses.

Vaccine manufacturers often employ complex technology entailing high costs for both the development and production of the vaccine. Concentration and purification of the vaccine is required, whether it is made from the whole bacteria, virus, other pathogenic organism or a sub-unit thereof. The high cost of purifying a vaccine in accordance with Food and Drug Administration (FDA) regulations makes oral vaccines prohibitively expensive to produce because they require ten to fifty times more than the regular quantity of vaccine per dose than a vaccine which is parenterally administered. Of all the viral vaccines being produced today only a few are being produced as oral vaccines.

According to FDA guidelines, efficacy of vaccines for humans must be demonstrated in animals by antibody development and by resistance to infection and disease upon challenge with the pathogen. When the safety and immunogenicity levels are satisfactory, FDA clinical studies are then conducted in humans. A small carefully controlled group of volunteers are enlisted from the general population to begin human trials. This begins the long and expensive process of testing which takes years before it can be determined whether the vaccine can be given to the general population. If the trials are successful, the vaccine may then be mass produced and sold to the public.

Even after these precautions are taken, problems can arise. With the killed virus vaccines, a there is always a chance that one of the live viruses has survived and vaccination may lead to isolated cases of the disease. Moreover, since both the killed and live attenuated types of virus vaccines are made from viruses grown in animal host cells, the vaccines are sometimes contaminated with cellular material from the animal host which can cause adverse, sometimes fatal, reactions in the vaccine recipient. Legal liability of the vaccine manufacturer for those who are harmed by a rare adverse reaction to a new or improved vaccine necessitates expensive insurance which ultimately adds to the cost of the vaccine.

Some vaccines have other disadvantages. Vaccines prepared from whole killed virus generally stimulate the development of circulating antibodies (IgM, IgG) thereby conferring a limited degree of immunity which usually requires boosting through the administration of additional doses of vaccine at specific time intervals. Live attenuated viral vaccines, while much more effective, have limited shelf-life and storage problems requiring maintaining vaccine refrigeration during delivery to the field.[1]

Efforts today are being made to produce less expensive vaccines which can be administered in a less costly manner. Recombinants or mutants can be produced that serve in place of live virus vaccines. The development of specific deletion mutants that alter the virus, but do not inactivate it, yield vaccines that can replicate but cannot revert to virulence.

Recombinant DNA techniques are being developed to insert the gene coding for the immunizing protein of one virus into the genome of a second, avirulent virus type that can be administered as the vaccine. Recombinant vaccines may be prepared by means of a vector virus such as vaccinia virus or by other methods of gene splicing. Vectors may include not only avirulent viruses but bacteria as well. A live recombinant hepatitis A vaccine has been constructed using attenuated *Salmonella typhimurium* as the delivery vector via oral administration.[1]

Various avirulent viruses have been used as vectors. The gene for hepatitis B surface antigen (HBsAg) has been introduced into a gene non-essential for vaccinia replication. The resulting recombinant virus has elicited an immune response to the hepatitis B virus in test animals. Additionally, researchers have used attenuated bacterial cells for expressing hepatitis B antigen for oral immunization. Importantly, when whole cell attenuated Salmonella expressing recombinant hepatitis antigen were fed to mice, anti-viral T and B cell immune responses were observed. These responses were generated after a single oral immunization with the bacterial cells resulting in high-titers of the antibody. See, e.g., "Expression of hepatitis B virus antigens in attenuated Salmonella for oral immunization," F. Schodel and H. Will, *Res. Microbiol.,* 141:831–837 (1990). Others have had similar success with oral administration routes for recombinant hepatitis antigens. See, e.g., M. D. Lubeck et al., "Immunogenicity and efficiacy testing in chimpanzees of an oral hepatitis B rs vaccine based on live recombinant adenovirus," *Proc. Natl. Acad. Sci.* 86:6763–6767 (1989); S. Kuriyama, et al., "Enhancing effects of oral adjuvants on anti-HBs responses induced by hepatitis B vaccine," *Clin. Exp. Immunol.* 72:383–389 (1988).

Other virus vectors may possess large genomes, e.g. the herpesvirus. The oral adenovirus vaccine has been modified so that it carries the HBsAg immunizing gene of the hepatitis B virus. Chimeric polio virus vaccines have been constructed of which the completely avirulent type 1 virus acts as a vector for the gene carrying the immunizing VP1 gene of type 3.[1]

Immunity to a pathogenic infection is based on the development of an immune response to specific antigens located on the surface of a pathogenic organism. For enveloped viruses, the important antigens are the surface glycoproteins. Glycosylation of viral surface glycoproteins is not always essential for antigenicity.[1] Unglycosylated herpesvirus proteins synthesized in bacteria have been shown to produce neutralizing antibodies in test animals.[1] However, where recombinant antigens such as HBsAg are produced in organisms requiring complex fermentative processes and machinery, the costs and access can be prohibitive.

Viral genes which code for a specific surface antigen that produces immunity in humans or animals, can be cloned into plasmids. The cloned DNA can then be expressed in prokaryotic or eukaryotic cells if appropriately engineered constructions are used. The immunizing antigens of hepatitis B virus,[2] foot and mouth,[3] rabies virus, herpes simplex virus, and the influenza virus have been successfully synthesized in bacteria or yeast cells.[1]

Animal and human subjects infected by a pathogen present an immune response when overcoming the invading microorganism. They do so by initiating at least one of three branches of the immune system: mucosal, humoral or cellular. Mucosal immunity results from the production of secretory IgA antibodies in the secretions that bathe mucosal surfaces in the respiratory tract, the gastrointestinal tract, the genitourinary tract and the secretory glands- McGhee, J. R. et al. Annals NY Acad. Sci.409:409 (1983). Mucosal antibodies act to prevent colonization of the pathogen on mucosal surfaces thus establishing a first line of defense against invasion. The production of mucosal antibodies can be initiated by either local immunization of the secretory gland or tissue or by presentation of the antigen to either the gut-associated lymphoid tissues (GALT; Peyer's Patches) or the bronchial-associated lymphoid tissue (BALT). Cebra, J. J. et al. Cold Spring Harbor Symp. Quant. Biol. 41:210 (1976); Bienenstock, J. M., Adv. Exp. Med. Biol. 107:53 (1978); Weisz-Carrington, P. et al., J. Immunol. 123:1705 (1979); McCaughan, G. et al., Internal Rev. Physiol. 28:131 (1983). Humoral immunity, on the other hand, results from the production of IgG and IgM antibodies in the serum, precipitating phagocytosis of invading pathogens, neutralization of viruses, or complement-mediated cytotoxicity against the pathogen. See, Hood et al. supra.

Others have noted that the induction of serum or mucosal antibody responses to orally administered antigens, however, may be problematic. Generally, such oral administration requires relatively large quantities of antigen since the amount of the antigen that is actually absorbed and capable of eliciting an immune response is usually low. Thus, the amount of antigen required for oral administration generally far exceeds that required for parenteral administration. de Aizpurua and Russell-Jones, J. Exp. Med. 167:440–451 (1988). However, it has been found that the systemic and mucosal immune systems may be stimulated by feeding low doses of certain classes of proteins. In particular, this may be achieved with proteins which share the property of being able to bind specifically to various glycolipids and glycoproteins located on the surface of the cells on the mucosal membrane. Such proteins, called "mucosal immunogens" have been found to include viral antigens such as viral hemagglutinin. Moreover, dose-response experiments comparing oral with intramuscular administration revealed that oral presentation of mucosal immunogens was remarkably efficient in eliciting a serum antibody response to the extent that the response elicited by oral presentation was only slightly lower than that elicited by intramuscular injection of the mucosal immunogen. de Aizpurua and Russell-Jones, supra.

The hypothesis proposed by these workers that such mucosal immunogens shared a common ability to bind glycosylated surface proteins on the mucosal membrane was at least partially confirmed by the inhibition of mucosal uptake of these mucosal immunogens by certain high levels of three specific sugars (galactose, lactose or sorbitol). Other sugars, fructose (the principal sugar found in many plant fruits) mannose and melibiose, did not inhibit mucosal immunogens from eliciting antibodies. de Aizpurua and Russell-Jones, supra. Others have found that certain sugars may, in fact, boost mucosal responses in the intestine. See, e.g., "Boosted Mucosal Immune Responsiveness in the Intestine by Actively Transported Hexose," S. Zhang and G. A. Castro, *Gastroenterol.,* accepted for publication).

Recent advances in genetic engineering have provided the requisite tools to transform plants to contain foreign genes. Plants that contain the transgene in all cells can then be regenerated and can transfer the transgene to their offspring in a Mendelian fashion.[4] Both monocotyledenous and dicotyledenous plants have been stably transformed. For example, tobacco, potato and tomato plants are but a few of the dicotyledenous plants which have been transformed by cloning a gene which encodes the expression of 5-enolpyruvyl-shikimate-3-phosphate synthase.[5]

Plant transformation and regeneration in dicotyledons by *Agrobacterium tumefaciens* (*A. tumefaciens*) is well documented. The application of the *Agrobacterium tumefaciens* system with the leaf disc transformation method[6] permits efficient gene transfer, selection and regeneration.

Monocotyledons have also been found to be capable of genetic transformation by *Agrobacterium tumefaciens* as well as by other methods such as direct DNA uptake mediated by PEG (polyethylene glycol), or electroporation. Successful transfer of foreign genes into corn[7] and rice,[8,9] as well as wheat and sorghum protoplasts has been demonstrated. Rice plants have been regenerated from untransformed and transformed protoplasts. New methods such as microinjection and particle bombardment may offer simpler and even more efficient means of transformation and regeneration of monocotyledons.[10]

Attempts to produce transgenic plants expressing bacterial antigens of *Escherichia coli* and of *Streptococcus mutans* have been made (*Curtiss and Ihnen,* WO 90/0248, Mar. 22, 1990). However, until the work of the present inventors, no transgenic plants had been constructed expressing viral antigens such as HBsAg.[72] In particular, until the work of the present inventors no such plants had been obtained which were capable of expressing viral antigens capable of eliciting an immune response as a mucosal immunogen. Moreover, until the work reported above no such plants had been obtained capable of producing particles which were antigenically and physically similar to the commercially available HBsAg viral antigens derived from human serum or recombinant yeast. However, none of these references provided the possibility of testing truly edible vaccines since all such studies were carried out in the classical tobacco test systems which plant tissues are not routinely digested by man or animal.

Thus, while prior approaches to obtaining less expensive and more accessible vaccines have been attempted, there remains a need to provide alternative sources of such vaccines for new antigens. Particularly, there remains need to provide alternative sources of vaccines which are incorporated by plants which are routinely included in human and animal diets. For instance, while vaccines such as HBsAg have been produced using antigen particles derived from human serum and recombinant yeast cells, both sources require greater expense and provide lower accessibility to technically underdeveloped nations. Furthermore, while certain bacterial antigens may be expressed in transgenic plants, until the work of the present inventors it was unknown whether antigens associated with human or animal viruses could be expressed in a form physically and antigenically similar to antigens used in commercial vaccines derived from human serum or recombinant yeasts. Similarly, while it is now possible to produce such recombinant antigens in tobacco plants by virtue of the present inventors work, no such antigens have been produced in plants routinely included in human and animal diets. In particular, prior art approaches have failed to provide such commercially viable antigen from plants made to express transgenic hepatitis B viral antigens. Viral antigens, anti-viral vaccines and transgenic plants expressing the same as well as methods of making and using such compositions of matter are needed which provide inexpensive and highly accessible sources of such medicines in common diet plants of man and animal.

SUMMARY OF THE INVENTION

Recombinant viral antigens, anti-viral vaccines and transgenic plants expressing the same are provided by the present invention. These compositions of matter are demonstrated by the present invention to be made and used by the methods of the invention in a manner which is potentially less expensive as well as more accessible to lower technological societies which rely chiefly on agricultural methods to provide essential raw materials.

More particularly, the present invention overcomes at least some of the disadvantages of the prior art by providing antigens produced in edible transgenic plants which antigens are antigenically and physically similar to those currently used in the manufacture of anti-viral vaccines derived from human serum or recombinant yeasts. In a preferred embodiment, these compositions of matter and methods provide transgenic plants, recombinant viral antigens and anti-viral vaccines related to the causative agent of human and animal viral diseases. The diseases of particular interest are those diseases in which the virus possesses an antigen capable, in at least the native state of the virus, of eliciting immune responses, particularly mucosal immune responses. In an embodiment of preference, the pathogen from which the antigen is derived is the hepatitis pathogen, and/in plants which are routinely included in human and animal diets.

In one embodiment, the compositions of matter and methods of the invention relate to oral vaccines introduced by consumption of a transgenic plant-derived antiviral vaccine. Such a plant derived vaccine may take various forms including purified and partially purified plant derived viral antigen as well as whole plant, whole plant parts such as fruits, leaves, stems, tubers as well as crude extracts of the plant or plant parts. In general, the preferred state of the composition of matter which is used to induce an immune response (i.e., whole plant, plant part, crude plant extract, partially purified antigen or extensively purified antigen) will depend upon the ability of the immunogen to elicit a mucosal response, the dosage level of the plant derived antigen required to elicit a mucosal response, and the need to overcome interference of mucosal immunity by other substances in the chosen composition of matter (i.e., sugars, pyrogens, toxins).

The present invention overcomes the deficiencies of the prior art by producing oral vaccines in one or more tissues of a transgenic plant, thereby availing large human and animal populations of an inexpensive means of vaccine production and administration. In a preferred embodiment the edible fruit, juice, grain, leaves, tubers, stems, seeds, roots or other plant parts of the vaccine producing transgenic plant is ingested by a human or an animal thus providing a very inexpensive means of immunization against disease. In a preferred embodiment, such plants will be plants routinely included in human and animal diets. Purification expense and adverse reactions inherent in existent vaccine production are thereby avoided. The invention also provides a novel and inexpensive source of antigen for more traditional vaccine delivery modes. These and other aspects of the present invention will become apparent from the following description and drawings.

In one embodiment, the oral vaccine of the present invention is produced in edible transgenic plants and then administered through the consumption of a part of those edible plants. A DNA sequence encoding the expression of a surface antigen of a pathogen is isolated and ligated into a plasmid vector containing selection markers. A promoter which regulates the production of the surface antigen in the transgenic plant is included in the same plasmid vector upstream from the surface antigen gene to ensure that the surface antigen is expressed in desired tissues of the plant. Preferably, the foreign gene is expressed in a portion of the plant that is edible by humans or animals. For some uses, such as with human infants, it is preferred that the edible food be a juice from the transgenic plant which can be taken orally.

In another embodiment, the vaccines (oral and otherwise) are provided by deriving recombinant viral antigens from the transgenic plants of the invention in at least a semi-purified form prior to inclusion into a vaccine. The present invention produces vaccines inexpensively. Further, vaccines from transgenic plants can not only be produced in the increased quantity required for oral vaccines but can be administered orally, thereby also reducing cost. The production of an oral vaccine in edible transgenic plants may avoid much of the time and expense required for FDA approval and regulation relating to the purification of the vaccine.

A principal advantage of the present invention is the humanitarian good which can be achieved through the production of inexpensive oral vaccines which can be used to vaccinate the populations of lesser developed countries who otherwise could not afford expensive oral vaccines manufactured under present methods or vaccines which require parenteral administration.

Thus, the invention provides for a recombinant mammalian viral protein expressed in a plant cell, which protein is known to elicit an antigenic response in a mammal in at least the native state of the virus. Preferably, the recombinant viral protein of the invention will also be one which is known to function as an antigen or immunogen (used interchangeably herein) as a recombinant protein when expressed in standard pharmaceutical expression systems such as yeasts or bacteria or where the viral protein is recovered from mammalian sera and shown to be antigenic. More preferably still, the antigenic/immunogenic protein of the invention will be a protein known to be antigenic/immunogenic when the protein as derived from the native virus, mammalian sera or from standard pharmaceutical expression systems, is used to induce the immune response through an oral mode of introduction. In its most preferred embodiment, the recombinant mammalian viral protein, known to be antigenic in its native state, will be a protein which upon expression in the plant cells of the invention, retains at least some portion of the antigenicity it possesses in the native state or as recombinantly expressed in standard pharmaceutical expression systems.

The immunogen of the invention is one derived from a mammalian virus and which is then expressed in a plant. In certain preferred embodiments, the mammalian virus from which the antigen is derived will be a pathogenic virus of the mammal. Thus, it is anticipated that some of the most useful plant-expressed viral immunogens will be those derived from a pathogenic virus of a mammal such as a human.

The immunogens of the invention are preferably produced in plants where at least a portion of the plant is edible. For the purposes of this invention, an edible plant or portion thereof is one which is not toxic when ingested by the mammal to be treated with the vaccine produced in the plant. Thus, for instance, many of the common food plants will be of particular utility when used in the compositions and methods of the invention. However, no nutritive value need be obtained when ingesting the plants of the invention in order for such a plant to be included within the types of the plants covered by the claimed invention. Moreover, in some cases, for instance in the domestic potato, a plant may still be considered edible as used herein, although some tissues of the plant, but not the entire plant, may be toxic when ingested (i.e., while potato tubers are not toxic and thus falling within the definitions of the claimed invention, the fruit of the potato is toxic when ingested). In such cases, such plants are still included within the definition of the claimed invention.

The immunogen of the invention, in a preferred embodiment, is a mucosal immunogen. For the purposes of the invention, a mucosal immunogen is an immunogen which has the ability to specifically prime the mucosal immune system. In a more highly preferred embodiment, the mucosal immunogens of the invention are those mucosal immunogens which prime the mucosal immune system and/or stimulate the humoral immune response in a dose-dependent manner, without inducing systemic tolerance and without the need for excessive doses of antigen. Systemic tolerance is defined herein as a phenomenon occurring with certain antigens which are repeatedly fed to a mammal resulting in a specifically diminished subsequent anti-antigen response. Of course, while the immunogens of the invention when used to induce a mucosal response may also induce a systemic tolerance, the same immunogen when introduced parenterally will typically retain its immunogenicity without developing tolerance.

A mucosal response to the immunogens of the invention is understood to include any response generated when the immunogen interacts with a mammalian mucosal membrane. Typically, such membranes will be contacted with the immunogens of the invention through feeding of the immunogen orally to a subject mammal. Using this route of introduction of the immunogen to the mucosal membranes provides access to the small intestine M cells which overlie the Peyer's Patches and other lymphoid clusters of the gut-associated lymphoid tissue (GALT). However, any mucosal membrane accessible for contact with the immunogens of the invention is specifically included within the definition of such membranes (e.g., mucosal membranes of the air passages accessible by inhaling, mucosal membranes of the terminal portions of the large intestine accessible by suppository, etc.).

Thus, the immunogens of the invention may be used to induce both mucosal as well as humoral responses. Where the immunogens of the invention are subjected to adequate levels of purification as further described herein, these immunogens may be introduced parenterally such as by muscular injection. Similarly, while preferred embodiments of the invention include feeding of relatively unpurified immunogen preparations (e.g., portions of edible plants, purees of such portions of plants, etc.), the introduction of the immunogen to stimulate the mucosal response may equally well occur through first subjecting the plant source of the immunogen to various purification procedures detailed herein or incorporated specifically by reference herein followed by introduction of such a purified immunogen through any of the modes discussed above for accessing the mucosal membranes.

The recombinant immunogens of the invention may represent the entire amino acid sequence of the native immunogen of the virus from which it is derived. However, in certain embodiments of the invention, the recombinant immunogen may represent only a portion of the native molecule's sequence. In either case, the immunogen may be fused to another peptide, polypeptide or protein to form a chimeric protein. The fusion of the molecules is accomplished either post-translationally through covalent bonding of one to another (e.g., covalent bonding of plant produced hepatitis B viral immunogen with whole hen egg lysozyme) or pre-translationally using recombinant DNA techniques (see e.g., supra discussion of poli virus vaccines), both of which methods are known well to those of skill in the art.

In certain embodiments, the immunogen of the invention will be an immunogen derived from a hepatitis virus. In particular embodiments, the hepatitis B virus surface antigen will be selected. Thus, in a highly preferred embodiment, a viral mucosal immunogen derived from a hepatitis virus is recombinantly expressed in a plant and is capable, in the native state of the virus or as a recombinant protein expressed in any standard pharmaceutical expression system, of eliciting an immune response, particularly a mucosal immune response.

In other embodiments of the invention, a transgenic plant comprising a plant expressing a recombinant viral immunogen derived from a mammalian virus is provided. For purposes of the invention, a transgenic plant is a plant expressing in at least some of the cells of the plant a recombinant viral immunogen. The transgenic plant of the invention, in preferred embodiments, is an edible plant, where the immunogen is a mucosal immunogen, or more preferably where a mucosal immunogen capable of binding a glycosylated molecule on the surface of a membrane of a mucosal cell, and in some embodiments where the immunogen is a chimeric protein. In other preferred embodiments, the transgenic plant of the invention will be a transgenic plant expressing a recombinant viral mucosal immunogen of hepatitis virus, where the mucosal immunogen is capable of eliciting an immune response, particularly a mucosal immune response, in the native state of the virus or as derived from standard pharmaceutical expression systems.

Also claimed herein are compositions of matter known as vaccines, where such vaccines are vaccines comprising a recombinant viral immunogen expressed in a plant. For the purposes of the invention, a vaccine is a composition of matter which, when contacted with a mammal, is capable of eliciting an immune response. As described above, certain preferred vaccines of the invention will be those vaccines useful against mammalian viruses as a mucosal immunogen, and more preferably as vaccines wherein the mucosal immunogen is capable of binding a glycosylated molecule on the surface of a membrane of a mucosal cell. In some embodiments, the vaccine may comprise a chimeric protein immunogen. In other embodiments, the vaccine of the invention will comprise an immunogen derived from a hepatitis virus. In still other preferred embodiments, the vaccine of the invention will comprise a mucosal immunogen of hepatitis virus expressed in a plant, where the mucosal immunogen is capable of eliciting an immune response, particularly a mucosal immune response, in the native state of the virus or as derived from standard pharmaceutical expression systems.

A food composition is also provided by the invention which comprises at least a portion of a transgenic plant capable of being ingested for its nutritional value, said plant comprising a plant expressing a recombinant viral immunogen. For the purposes of the invention, a plant or portion thereof is considered to have nutritional value when it provides a source of metabolizable energy, supplementary or necessary vitamins or co-factors, roughage or otherwise beneficial effect upon ingestion by the subject mammal. Thus, where the mammal to be treated with the food is an herbivore capable of bacterial-aided digestion of cellulose, such a food might be represented by a transgenic monocot grass. Similarly, although transgenic lettuce plants do not substantially contribute energy sources, building block molecules such as proteins, carbohydrates or fats, nor other necessary or supplemental vitamins or cofactors, a lettuce plant transgenic for the viral immunogen of a mammalian virus used as a food for that mammal would fall under the definition of a food as used herein if the ingestion of the lettuce contributed roughage to the benefit of the mammal, even if the mammal could not digest the cellulosic content of lettuce.

As described in the compositions of matter recited above, certain preferred foods of the invention will include foods where the immunogen is a mucosal immunogen, or where mucosal immunogen is capable of binding a glycosylated molecule on the surface of a membrane of a mucosal cell, or where the immunogen is a chimeric protein or where, the immunogen is an immunogen derived from a hepatitis virus. Thus, in a highly preferred embodiment, the food of the claimed invention will comprise at least a portion of a transgenic plant capable of being ingested for its nutritional value, where the plant expresses a recombinant viral mucosal immunogen of hepatitis virus, and where the mucosal immunogen is capable of binding a glycosylated molecule on a surface of a membrane of a mucosal cell. In any case, the foods of the invention may be those portions of a plant including the fruit, leaves, stems, roots, or seeds of said plant.

Of particular importance to the compositions and methods of the claimed invention are certain plasmid constructions useful in obtaining the plants, immunogens, vaccines, and foods of the invention. Thus, plasmid vectors for transforming a plant are claimed comprising a DNA sequence encoding a mammalian viral immunogen and a plant-functional promoter operably linked to the DNA sequence capable of directing the expression of the immunogen in said plant. In certain embodiments, the plasmid vector further comprises a selectable or scorable marker gene to facilitate the detection of the transformed cell or plant. In certain embodiments, plasmid vector of the invention will comprise the plant promoter of cauliflower mosaic virus, CaMV35S. As with other compositions of matter described above, certain preferred embodiments of the plasmid vector of the invention will be those where the plant transformed by the plasmid vector is edible, or where the immunogen encoded by the plasmid vector is a mucosal immunogen, or more preferably where the immunogen encoded by the plasmid vector is capable of eliciting an immune response, particularly a mucosal immune response, in the native state of the virus or as derived from standard pharmaceutical expression systems, or where the encoded immunogen is a chimeric protein, or where the encoded immunogen is an immunogen derived from a hepatitis virus. Thus, in a highly preferred embodiment, the plasmid vector of the invention useful for transforming a plant comprises a DNA sequence encoding a mucosal immunogen of hepatitis virus, where the mucosal immunogen is capable of eliciting an immune response, particularly a mucosal immune response, in the native state of the virus or as derived from standard pharmaceutical expression systems and where a plant-functional promoter is operably linked to the DNA sequence capable of directing the expression of the immunogen in the plant. In a very similar embodiment, the invention provides for DNA fragments useful for microparticle bombardment transformation of a plant.

Methods for constructing transgenic plant cells are also provided by the invention comprising the steps of constructing a plasmid vector or a DNA fragment by operably linking a DNA sequence encoding a viral immunogen to a plant-functional promoter capable of directing the expression of the immunogen in the plant and then transforming a plant cell with the plasmid vector or DNA fragment. Where preferred, the method may be extended to produce transgenic plants from the transformed cells by including a step of regenerating a transgenic plant from the transgenic plant cell.

A method for producing a vaccine is also provided by the claimed invention, comprising the steps of constructing a plasmid vector or a DNA fragment by operably linking a DNA sequence encoding a viral immunogen to a plant-functional promoter capable of directing the expression of the immunogen in the plant, transforming a plant cell with the plasmid vector or DNA fragment, and then recovering the immunogen expressed in the plant cell for use as a vaccine. Again, where preferred, the method provides for an additional step prior to recovering the immunogen for use as a vaccine, of regenerating a transgenic plant from the transgenic plant cell.

The recovery of the immunogen from the plant cell or whole plant may take several embodiments. In one such embodiment, the method of recovering the immunogen of the invention is accomplished by obtaining an extract of the plant cell or whole plant or portions thereof. In embodiments where whole plants are regenerated by the methods of the invention, the recovery step may comprise merely harvesting at least a portion of the transgenic plant.

The methods of the invention provide for any of a number of transformation protocols in order to transform the plant cells and plants of the invention. While certain preferred embodiments described below utilize particular transformation protocols, it will be understood by those of skill in the art that any transformation method may be utilized with in the definitions and scope of the invention. Such methods include microinjection, polyethylene glycol mediated uptake, and electroporation. Thus, certain preferred methods will utilize an Agrobacterium transformation system, in particular, where the Agrobacterium system is an *Agrobacterium tumefaciens*-Ti plasmid system. In other preferred methods, the plant cell is transformed utilizing a microparticle bombardment transformation system.

Plants of particular interest in the methods of the invention include tomato plants and tobacco plants as will be described in more detail in the examples to follow. However, it will be understood by those of skill in the art of plant transformation that a wide variety of plant species are amenable to the methods of the invention. All such species are included within the definitions of the claimed invention including both dicotyledon as well as monocotyledon plants.

As will be described in greater detail in the examples to follow, the methods of the invention by which plants are transformed may utilize plasmid vectors which are binary vectors. In other embodiments, the methods of the invention may utilize plasmids which are integrative vectors. In a highly preferred embodiment, the methods of the invention will utilize the plasmid vector pB121.

Methods of administering any of the vaccines of the invention are also provided. In certain general embodiments, such methods comprise administering a therapeutic amount of the vaccine to a mammal. In more specific embodiments, these methods entail introduction of the vaccine either parenterally or non-parenterally into a mammalian subject. Where a non-parenteral introduction mode is selected, certain preferred embodiments will comprise oral introduction of the vaccine into said mammal. Whichever mode of introduction of the vaccine to the mammalian subject is selected, it will be understood by those skilled in the art of vaccination that the selected mode must achieve vaccination at the lowest dose possible in a dose-dependent manner and by so doing elicit serum and/or secretory antibodies against the immunogen of the vaccine with minimal induction of systemic tolerance. Where a mucosal route of vaccination is selected, care should be taken to introduce the vaccine into the gut lumen of the mammal at low dosages and in forms which minimize the simultaneous introduction of interfering compounds such as galactose and galactose-like saccharides.

In preferred embodiments, methods are provided by the invention of administering an edible portion of a transgenic plant, which transgenic plant expresses a recombinant viral immunogen, to a mammal as an oral vaccine against a virus from which said immunogen is derived. These methods comprise harvesting at least an edible portion of the transgenic plant, and feeding the harvested plant or portion thereof to a mammal in a suitable amount to be therapeutically effective as an oral vaccine in the mammal.

Similarly, the invention provides for methods of producing and administering an oral vaccine, comprising the steps of constructing a plasmid vector or DNA fragment by operably linking a DNA sequence encoding a viral immunogen to a plant-functional promoter capable of directing the expression of the immunogen in a plant, transferring the plasmid vector into a plant cell, regenerating a transgenic plant from the cell, harvesting an edible portion of the regenerated transgenic plants, and feeding the edible portion of the plant to a mammal in a suitable amount to be therapeutically effective as an oral vaccine. It is this embodiment that will be of particular utility in underdeveloped countries committed to agricultural raw products as a main source of most necessities.

Other objects and advantages of the invention will appear from the following description.

BRIEF DESCRIPTION OF THE DRAWINGS

For a detailed description of the preferred embodiment of the invention, reference will now be made to the accompanying drawings wherein.

DESCRIPTION OF THE PREFERRED EMBODIMENT

Figure 1:
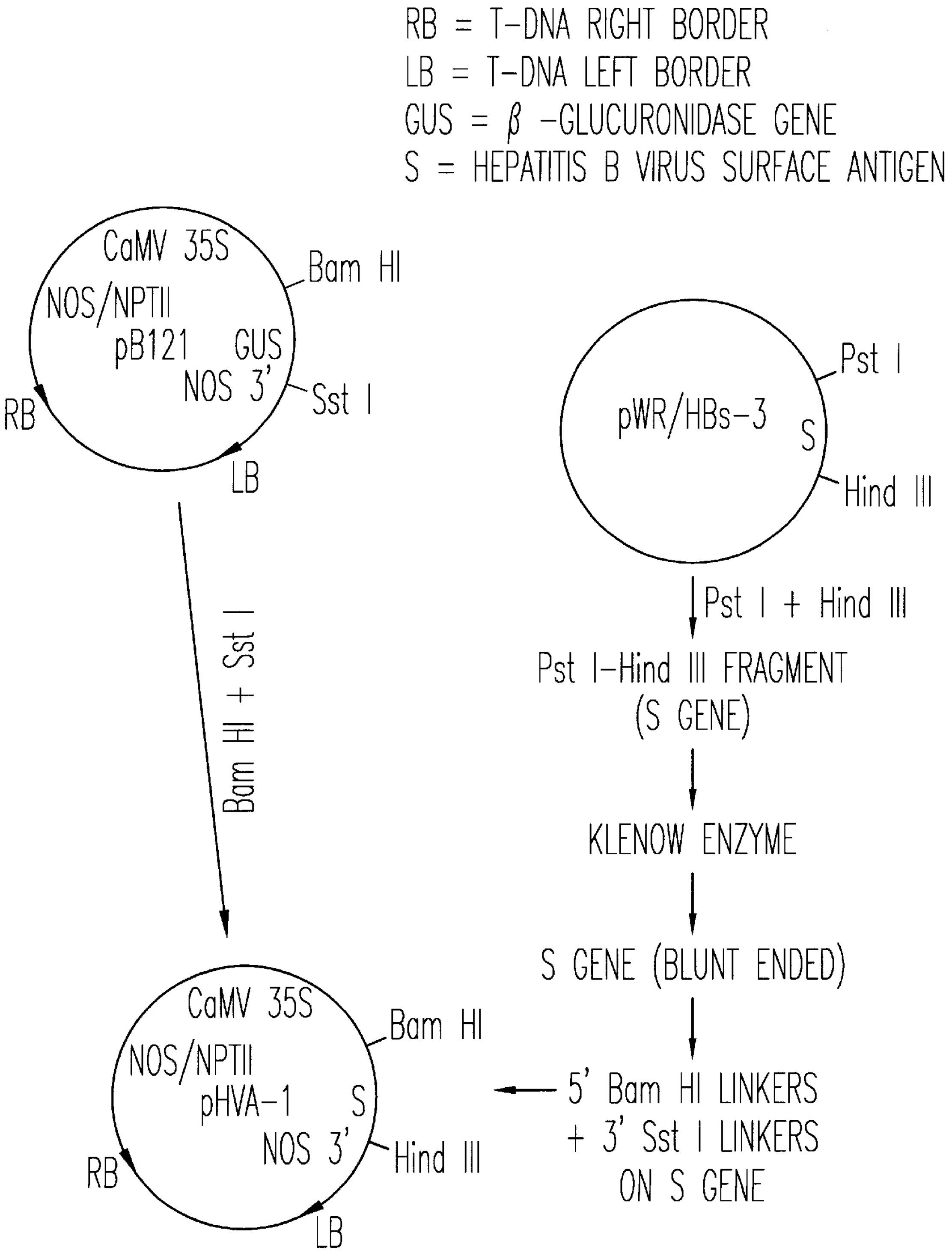
FIG. 1 is a diagrammatic plasmid construct illustrating the construction of the plasmid vector pHVA-1 containing the HBsAg gene for producing the HBsAg antigen in a plant.

The present invention has several components which include: using recombinant DNA techniques to create a plasmid vector which contains a DNA segment encoding one or more antigenic proteins which confer immunity in a human or an animal to a particular disease and for the expression of antigenic protein(s) in desired tissues of a plant; selecting an appropriate host plant to receive the DNA segment encoding antigenic protein(s) and subsequently produce the antigenic protein(s); transferring the DNA segment encoding the antigenic protein(s) from the plasmid vector into the selected host plant; regenerating the transgenic plant thereby producing plants expressing the antigenic protein(s) which functions as a vaccine(s); and administering an edible part of the transgenic plant containing the antigenic protein(s) as an oral vaccine to either a human or an animal by the consumption of a transgenic plant part. The present invention thereby provides for the production of a transgenic plant which when consumed as food, at least in part, by a human or an animal causes an immune response. This response is characterized by resistance to a particular disease or diseases. The response is the result of the production in the transgenic plant of antigenic protein(s). The production of the antigenic protein(s) is the result of stable genetic integration into the transgenic plant of DNA regions designed to cause regulated expression of antigenic protein(s) in the transgenic plants.

Vaccine(s) and Their Administration

The present invention may be used to produce any type vaccine effective in immunizing humans and animals against diseases. Viruses, bacteria, fungi, and parasites that cause disease in humans and animals can contain antigenic protein(s) which can confer immunity in a human or an animal to the causative pathogen. A DNA sequence encoding any of these viral, bacterial, fungal or parasitic antigenic proteins may be used in the present invention.

Mutant and variant forms of the DNA sequences encoding a antigenic protein which confers immunity to a particular virus, bacteria, fungus or parasite in an animal (including humans) may also be utilized in this invention. For example, expression vectors may contain DNA coding sequences which are altered so as to change one or more amino acid residues in the antigenic protein expressed in the plant, thereby altering the antigenicity of the expressed protein. Expression vectors containing a DNA sequence encoding only a portion of an antigenic protein as either a smaller peptide or as a component of a new chimeric fusion protein are also included in this invention.

The present invention is advantageously used to produce viral vaccines for humans and animals. The following table sets form a list of vaccines now used for the prevention of viral diseases in humans.

| Disease | Source of Vaccine | Condition of Virus | Route of Administration |
|---|---|---|---|
| Poliomyelitis | Tissue culture human diploid cell line, monkey kidney) | Live attenuated<br>Killed | Oral<br>Subcutaneous |
| Measles | Tissue culture (chick embryo) | Live attenuated | Subcutaneous |
| Mumps | Tissue culture (chick embryo) | Live attenuated | Subcutaneous |
| Rubella | Tissue culture (duck embryo, rabbit, or human diploid) | Live attenuated | Subcutaneous |
| Small pox | Lymph from calf or sheep | Live vaccinia | Intradermal |
| Yellow Fever | Tissue cultures and eggs | Live attenuated | Subcutaneous |
| Viral hepatitis B | Purified HBsAg from "health" carriers<br>Recombinant HBsAg from yeast | Live attenuated<br>Subunit | Subcutaneous<br>Subcutaneous |
| Influenza | Highly purified or subviral forms (chick embryo) | Killed | Subcutaneous |
| Rabies | Human diploid cell cultures | Killed | Subcutaneous |
| Adenoviral infections | Human diploid cell cultures | Live attenuated | Oral |
| Japanese B encephalitis | Tissue culture (hamster kidney) | Killed | Subcutaneous |
| Varicella | Human diploid cell cultures | Live attenuated | Subcutaneous |

The present invention is also advantageously used to produce vaccines for animals. Vaccines are available to immunize pets and production animals. Diseases such as: canine distemper, rabies, canine hepatitis, parvovirus, and feline leukemia may be controlled with proper immunization of pets. Viral vaccines for diseases such as: Newcastle, Rinderpest, hog cholera, blue tongue and foot-mouth can control disease outbreaks in production animal populations, thereby avoiding large economic losses from disease deaths. Prevention of bacterial diseases in production animals such as: brucellosis, fowl cholera, anthrax and black leg through the use of vaccines has existed for many years. Today new recombinant DNA vaccines, e.g. rabies and foot and mouth, have been successfully produced in bacteria and yeast cells and can facilitate the production of a purified vaccine containing only the immunizing antigen. Veterinary vaccines utilizing cloned antigens for protozoans and helminths promise relief from parasitic infections which cripple and kill.

The oral vaccine produced by the present invention is administered by the consumption of the foodstuff which has been produced from the transgenic plant producing the antigenic protein as the vaccine. The edible part of the plant is used as a dietary component while the vaccine is administered in the process.

The present invention allows for the production of not only a single vaccine in an edible plant but for a plurality of vaccines into one foodstuff. DNA sequences of multiple antigenic proteins can be included in the expression vector used for plant transformation, thereby causing the expression of multiple antigenic amino acid sequences in one transgenic plant. Alternatively, a plant may be sequentially or simultaneously transformed with a series of expression vectors, each of which contains DNA segments encoding one or more antigenic proteins. For example, there are five or six different types of influenza, each requiring a different vaccine. A transgenic plant expressing multiple antigenic protein sequences can simultaneously elicit an immune response to more than one of these strains, thereby giving disease immunity even though the most prevalent strain is not known in advance.

Vaccines produced in accordance with the present invention may also be incorporated into the feed of animals. This represents an important means to produce lower cost disease prevention for pets, production animals, and wild species.

While the vaccines of the present invention will be preferably utilized directly as oral vaccines of the transgenic plant material, immunogenic compositions derived from the transgenic plant materials suitable for use as more traditional immune vaccines may be readily prepared from the transgenic plant materials described herein. Preferably, such immune compositions will comprise a material purified from the transgenic plant. Purification of the antigen may take many forms known well to those of skill in the art, in particular such purifications will likely track closely the purification techniques used successfully in obtaining viral antigen particles from recombinant yeasts (i.e., those containing HBsAg). In one embodiment, detailed in the examples to follow, HBsAg viral protein-containing particles, similar in many respects to those obtained from recombinant yeasts, were purified from transformed tobacco plants using a particular purification procedure. Whatever initial purification scheme is utilized, the purified material will also be extensively dialyzed to remove undesired small molecular weight molecules (i.e., sugars, pyrogens) and/or lyophilization of the thus purified material for more ready formulation into a desired vehicle.

The preparation of vaccines is generally well understood in the art (e.g., those derived from fermentative yeast cells known well in the art of vaccine manufacture cite to Valenzuela et al *Nature* 298, 347–350 (1982), as exemplified by U.S. Pat. Nos. 4,608,251; 4,601,903; 4,599,231; 4,599,230; 4,596,792; and 4,578,770, all incorporated herein by reference. Typically, such vaccines are prepared as injectables, either as liquid solutions or suspensions. Solid forms suitable for solution in, or suspension in, liquid prior to injection may also be prepared.

The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjuvants which enhance the effectiveness of the vaccines.

The vaccines are conventionally administered parenterally, by injection, for example, either subcutaneously or intramuscularly. Additional formulations which are suitable for other modes of administration include suppositories and, in some cases, oral formulations or aerosols. For suppositories, traditional binders and carriers may include, for example, polyalkalene glycols or triglycerides: such suppositories may be formed from mixtures containing the active ingredient in the range of 0.5% to 10%, preferably 1–2%. Oral formulations other than edible plant portions described in detail herein include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain 10–95% of active ingredient, preferably 25–70%.

In many instances, it will be desirable to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1–5 years, usually three years, will be desirable to maintain protective levels of the antibodies.

The course of the immunization may be followed by assays for antibodies for the supernatant antigens. The assays may be performed by labeling with conventional labels, such as radionuclides, enzymes, fluorescers, and the like. These techniques are well known and may be found in a wide variety of patents, such as U.S. Pat. Nos. 3,791,932; 4,174,384 and 3,949,064, as illustrative of these types of assays.

Host Plant Selection

A variety of plant species have been genetically transformed with foreign DNA, using several different gene insertive techniques.[10,22-27,29-32] Since important progress is being made to clone DNA coding regions for vaccine antigens for parasitic tropical diseases and veterinary parasitic diseases[11-21] the present invention, will have important means of low cost production of vaccines in a form easily used for animal treatment.

Since many edible plants used by humans for food or as components of animal feed are dicotyledenous plants, it is preferred to employ dicotyledons in the present invention, although monocotyledon transformation is also applicable especially in the production of certain grains useful for animal feed.

The host plant selected for genetic transformation preferably has edible tissue in which the antigenic protein, a proteinaceous substance, can be expressed. Thus, the antigenic protein is expressed in a part of the plant, such as the fruit, leaves, stems, seeds, or roots, which may be consumed by a human or an animal for which the vaccine is intended. Although not preferred, a vaccine may be produced in a non-edible plant and administered by one of various other known methods of administering vaccines.

Various other considerations are made in selecting the host plant. It is sometimes preferred that the edible tissue of the host plant not require heating prior to consumption since the heating may reduce the effectiveness of the vaccine for animal or human use. Also, since certain vaccines are most effective when administered in the human or animal infancy period, it is sometimes preferred that the host plant express the antigenic protein which will function as a vaccine in the form of a drinkable liquid.

Plants which are suitable for the practice of the present invention include any dicotyledon and monocotyledon which is edible in part or in whole by a human or an animal such as, but not limited to, carrot, potato, apple, soybean, rice, corn, berries such as strawberries and raspberries, banana and other such edible varieties. It is particularly advantageous in certain disease prevention for human infants to produce a vaccine in a juice for ease of administration to humans such as tomato juice, soy bean milk, carrot juice, or a juice made from a variety of berry types. Other foodstuffs for easy consumption might include dried fruit.

Methods of Gene Transfer into Plants

There are various methods of introducing foreign genes into both monocotyledenous and dicotyledenous plants.[33,34] The principle methods of causing stable integration of exogenous DNA into plant genomic DNA include the following approaches: 1) Agrobacterium—mediated gene transfer;[35,36, 37,53] 2) direct DNA uptake,[38] including methods for direct uptake of DNA into protoplasts,[8] DNA uptake induced by brief electric shock of plant cells,[41,42] DNA injection into plant cells or tissues by particle bombardment,[39,44-46] by the use of micropipette systems,[43,47,48] or by the direct incubation of DNA with germinating pollen;[40,49] or 3) the use of plant virus as gene vectors.[33,51]

The Agrobacterium system includes the use of plasmid vectors that contain defined DNA segments that integrate into the plant genomic DNA. Methods of inoculation of the plant tissue vary depending upon the plant species and the Agrobacterium delivery system. A widely used approach is the leaf disc procedure which can be performed with any tissue explant that provides a good source for initiation of whole plant differentiation.[6] The Agrobacterium system is especially viable in the creation of transgenic dicotyledenous plants.

As listed above there are various methods of direct DNA transfer into plant cells. In electroporation, the protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals or tungsten particles, and the microprojectiles are physically accelerated into cells or plant tissues.

The last principle method of vector transfer is the transmission of genetic material using modified plant viruses. DNA of interest is integrated into DNA viruses, and these viruses are used to infect plants at wound sites.

In the preferred embodiment of the present invention, the Agrobacterium—Ti plasmid system is utilized.[53] The tumor-inducing (Ti) plasmids of *A. tumefaciens* contain a segment of plasmid DNA called transforming DNA (T-DNA) which is transferred to plant cells where it integrates into the plant host genome. The construction of the transformation vector system has two elements. First, a plasmid vector is constructed which replicates in *Escherichia coli* (*E. coli*). This plasmid contains the DNA encoding the protein of interest (an antigenic protein in this invention); this DNA is flanked by T-DNA border sequences that define the points at which the DNA integrates into the plant genome. Usually a gene encoding a selectable marker (such as a gene encoding resistance to an antibiotic such as Kanamycin) is also inserted between the left border (LB) and right border (RB) sequences; the expression of this gene in transformed plant cells gives a positive selection method to identify those plants or plant cells which have an integrated T-DNA region.[52,53] The second element of the process is to transfer the plasmid from *E. coli* to Agrobacterium. This can be accomplished via a conjugation mating system, or by direct uptake of plasmid DNA by Agrobacterium. For subsequent transfer of the T-DNA to plants, the Agrobacterium strain utilized must contain a set of inducible virulence (vir) genes which are essential for T-DNA transfer to plant cells.[53,54]

Those skilled in the art should recognize that there are multiple choices of Agrobacterium strains and plasmid construction strategies that can be used to optimize genetic transformation of plants. They will also recognize that *A. tumefaciens* may not be the only Agrobacterium strain used. Other Agrobacterium strains such as *A. rhizogenes* might be more suitable in some applications.

Methods of inoculation of the plant tissue vary depending upon the plant species and the Aarobacterium delivery system. A very convenient approach is the leaf disc procedure which can be performed with any tissue explant that provides a good source for initiation of whole plant differentiation. The addition of nurse tissue may be desirable under certain conditions. Other procedures such as the in vitro transformation of regenerating protoplasts with *A. tumefaciens* may be followed to obtain transformed plant cells as well.[33,53]

This invention is not limited to the Agrobacterium-Ti plasmid system but should include any direct physical method of introducing foreign DNA into the plant cells, transmission of genetic material by modified plant viruses, and any other method which would accomplish foreign DNA transfer into the desired plant cells.

Promoters

Once the host plant has been selected and the method of gene transfer into the plant determined, a constitutive, a developmentally regulated, or a tissue specific promoter for the host plant is selected so that the foreign protein is expressed in the desired part(s) of the plant.

Promoters which are known or found to cause transcription of a foreign gene in plant cells can be used in the present invention. Such promoters may be obtained from plants or viruses and include, but are not necessarily limited to: the 35S promoter of cauliflower mosaic virus (CaMV) (as used herein, the phrase "CaMV 35S" promoter includes variations of CaMV 35S promoter, e.g. promoters derived by means of ligations with operator regions, random or controlled mutagenesis, etc.); promoters of seed storage protein genes such as Zma10Kz or Zmag12 (maize zein and glutelin genes, respectively), light-inducible genes such as ribulose bisphosphate carboxylase small subunit (rbcS), stress induced genes such as alcohol dehydrogenase (Adh1), or "housekeeping genes" that express in all cells (such as Zmaact, a maize actin gene).[4,55] This invention can utilize promoters for genes which are known to give high expression in edible plant parts, such as the patatin gene promoter from potato.[56]

The plasmid constructed for plant transformation also usually contains a selectable or scorable marker gene. Numerous genes for this purpose have been identified.[54,57]

The following are examples of the production of a vaccine for hepatitis B in a host transgenic tomato and tobacco plant and are presented to describe a preferred embodiment and the utility of the present invention but should not be construed as limiting the claims thereof.

The DNA coding sequence for the hepatitis B surface antigen was selected for expression in a transgenic plant as Hepatitis B virus is one of the most widespread viral infections of humans which causes acute and chronic hepatitis and heptocellular carcinoma.[71] Tomato and tobacco plants were selected as the host plants to produce the hepatitis B recombinant surface antigen as examples of antigenic protein production in different plant parts. Expression of HbsAg in tobacco and tomato plants was accomplished by the method of Mason, H. S. Lam, and Arntzen, C. J., Proceedings of the National Academy of Sciences, U.S.A. Vol. 89, 11745–11749(1992), herein incorporated by reference.

EXAMPLE I

A. Construction of Hepatitis B Surface Antigen Expression Vector pHVA-1

Referring initially to the diagrammatic plasmid construct illustrated in FIG. 1, the DNA sequence encoding for HBsAg contained within restriction endonuclease sites Pst I-Hind III on plasmid pWR/HBs-3 was excised and subsequently ligated into the unique Bam HI-Sst I site of the excised beta-glucuronidase (GUS) gene on plasmid pB121 to construct the binary vector plasmid pHVA-1.

Plasmid pB121, obtained from Clonetech Laboratories, Inc., Palo Alto, Calif., has cleavage sites for the restriction endonucleases Bam HI and Sst I located between the CaMV 35S promoter and the GUS structural gene initiation sequence and between the GUS gene termination sequence and the NOS polyadenylation signals, respectively. Plasmid pB121 was selected since the GUS structural gene can be excised from the plasmid using Bam HI and Sst I, another structural gene encoding an antigenic protein can be inserted, and the new gene will be functionally active in plant gene expression. Plasmid pB121 also contains a NPT II gene encoding neomycin phosphotransferase II; this is an enzyme that confers Kanamycin resistance when expressed in transformed plant cells, thereby allowing the selection of cells and tissues with integrated T-DNA. The NPT II gene is flanked by promoter and polyadenylation sequences from a Nopaline synthase (NOS) gene.

The HBsAg DNA coding sequence[64,65] was isolated from the plasmid pWR/HBs-3 (constructed at the Institute of Cell Biology in China) as a Pst I - Hind III fragment. This fragment was digested with Klenow enzyme to create blunt ends; the resultant fragment was ligated at the 5' end with Bam H1 linkers and at the 3' end with Sst 1 linkers, and then inserted into the pB121 plasmid at the site where the GUS coding sequence had been excised, thereby creating plasmid pHVA-1 as shown in FIG. 1.

Figure 2:
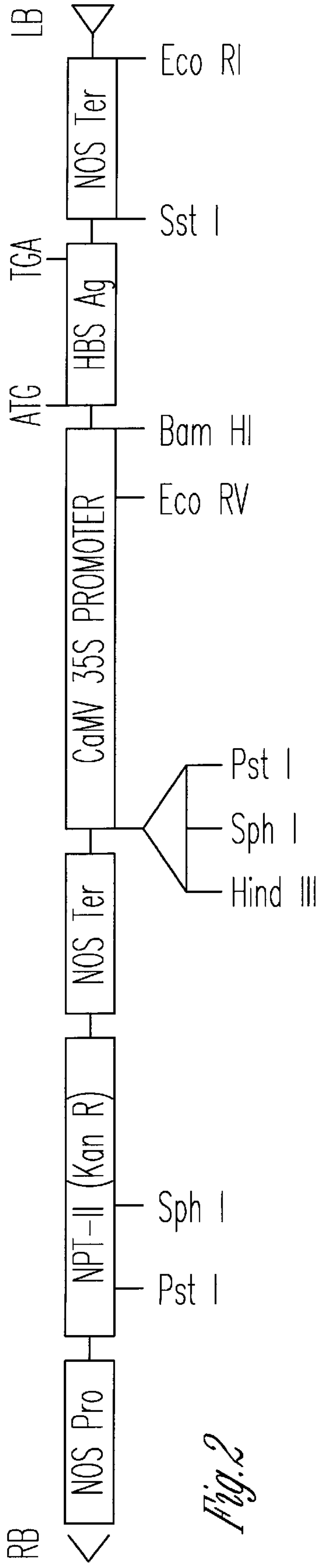
FIG. 2 is a map of the coding sequence for two structural genes and their regulatory elements in the plasmid pHVA-1.

The plasmid vector pHVA-1 then contains 1) a neomycin phosphotransferase II (NPT II) gene which provides the selectable marker for kanamycin resistance; 2) a HBsAg gene regulated by a cauliflower mosaic virus (CaMV 35S) promoter sequence; and 3) right and left T-DNA border sequences which effectively cause the DNA sequences for the NOS and HBsAg genes to be transferred to plant cells and integrated into the plant genome. The diagrammatic structure of pHVA-1 is shown in FIG. 2.

B. Transfer of Binary Vector, pHVA-1, to *A. tumefaciens*

Plasmid pHVA-1, containing the HBsAg gene, was transferred to *A. tumefaciens* strain LBA4404 obtained from Clontech Laboratories, Inc. This strain is widely used since it is "disarmed"; that is, it has intact vir genes, but the T-DNA region has been removed by in vivo deletion techniques. The vir genes work in trans to mediate T-DNA transfer to plants from the plasmid pHVA-1.

*A. tumefaciens* was cultured in AB medium[58] containing two-tenths milligrams per milliliter (0.2 mg/ml) streptomycin until the optical density (O.D.) at six hundred nanometers (600 nm) of the culture reaches about five tenths (0.5). The cells are then centrifuged at 2000 times gravity (2000XG) to obtain a bacterial cell pellet. The Agrobacterium pellet was resuspended in one milliliter of ice cold twenty millimolar calcium chloride (20 mM $CaCl_2$). Five tenths microgram (0.5 $\mu$g) of plasmid pHVA-1 DNA was added to two tenths milliliters (0.2 ml) of the calcium chloride suspension of *A. tumefaciens* cells in a one and five tenths milliliter (1.5 ml) microcentrifuge tube and incubated on ice for sixty minutes. The plasmid pHVA-1 DNA and *A. tumefaciens* cells mixture was frozen in liquid nitrogen for one minute, thawed in a twenty-five degree Celsius (25° C.) water bath, and then mixed with five volumes or one milliliter (1 ml) of rich MGL medium.[58] The plasmid pHVA-1 and *A. tumefaciens* mixture was then incubated at twenty-five degrees Celsius (25° C.) for four hours with gentle shaking. The mixture was plated on LB, luria broth,[58] agar medium containing fifty micrograms per milliliter (50 $\mu$g/ml) kanamycin. Optimum drug concentration may differ depending upon the Agrobacterium strain in other experiments. The plates were incubated for three days at twenty-five degrees Celsius (25° C.) before selection of resultant colonies which contained the transformed Agrobacterium harboring the pHAV-1 plasmids.

The presence of pHVA-1 DNA in the transformed Agrobacterium culture was verified by restriction mapping of the plasmid DNA purified by alkaline lysis of the bacterial cells.[59]

C. Plant Transformation by *A. tumefaciens* Containing the HBsAg Gene as Part of the Ti Vector System The technique for in vitro transformation of plants by the Agrobacterium-Ti plasmid system is based on cocultivation of plant tissues or cells and the transformed Agrobacterium for about two days with subsequent transfer of plant materials to an appropriate selective medium. The material can be either protoplast, callus or organ tissue, depending upon the plant species. Organ cocultivation with leaf pieces is a convenient method.

Leaf disc transformation was performed in accordance with the procedure of Horsch et al[6]. Tomato and tobacco seedlings were grown in flats under moderate light and temperature and low humidity to produce uniform, healthy plants of ten to forty centimeters in height. New flats were started weekly and older plants were discarded. The healthy, unblemished leaves from the young plants were harvested and sterilized in bleach solution containing ten per cent (10%) household bleach (diluted one to ten from the bottle) and one tenth per cent (0.1 %) Tween 20 or other surfactant for fifteen to twenty minutes with gentle agitation. The leaves were then rinsed three times with sterile water. The leaf discs were then punched with a sterile paper punch or cork borer, or cut into small strips or squares to produce a wounded edge.

Leaf discs were precultured for one to two days upside down on MS104[6] medium to allow initial growth and to eliminate those discs that were damaged during sterilization or handling. Only the leaf discs which showed viability as evidenced by swelling were used for subsequent inoculation. The *A. tumefaciens* containing pHVA-1 which had been grown in AB medium were diluted one to twenty with MSO[6] for tomato inoculation and one to ten for tobacco discs. Leaf discs were inoculated by immersion in the diluted transformed *A. tumefaciens* culture and cocultured on regeneration medium MS 104[6] medium for three days. Leaf discs were then washed with sterile water to remove the free *A. tumefaciens* cells and placed on fresh MS selection medium which contained three hundred micrograms per milliliter (300 $\mu$g/ml) of kanamycin to select for transformed plants cells and five hundred micrograms per milliliter (500 $\mu$g/ml) carbenicillin to kill any remaining *A. tumefaciens*. The leaf discs were then transferred to fresh MS selection medium at two week intervals. As shoots formed at the edge of the leaf discs and grew large enough for manual manipulation, they were excised (usually at three to six weeks after cocultivation with transformed *A. tumefaciens*) and transferred to a root-inducing medium, e.g. MS rooting medium.[6] As roots appeared the plantlets were either allowed to continue to grow under sterile tissue culture conditions or transferred to soil and allowed to grow in a controlled environment chamber.

D. Selection of Genetically-Engineered Plants Which Express HBsAg

Approximately three months (nine months for tomato fruit assays) after the initial cocultivation of the putative HBsAg expressing tomato plants (HB-plants) with *A. tumefaciens,* they were tested for the presence of HBsAg.

1. Biochemical and Immunochemical Assays

Root, stem, leaf and fruit samples of the plants were excised. Each tissue was homogenized in a buffered solution, e.g. one hundred millimolar sodium phosphate (100 mM), pH 7.4 containing one millimolar ethylenediamine tetraacetate (1.0 mM EDTA) and five-tenths millimolar phenylmethylsulfonyl fluoride (0.5 mM PMSF) as a proteinase inhibitor. The homogenate was centrifuged at five thousand times gravity (5000XG) for ten minutes. A small aliquot of each supernatant was then reserved for protein determination by the Lowry method. The remaining supernatant was used for the determination of the level of HBsAg expression using two standard assays: (a) a HBsAg radioimmunoassay, the reagents for which were purchased from Abbott Laboratories and (b) immunoblotting using a previously described method of Peng and Lam[61] with a monoclonal antibody against anti-HBsAg purchased from Zymed Laboratories. Depending upon the level of HBsAg expression in each tissue, the supernatant may have been partially purified using a previously described affinity chromatographic method of Pershing et al[62] using monoclonal antibody against HBsAg bound to commercially available Affi-Gel 10 gel from Bio-Rad Laboratories, Richmond, Calif. The purified supernatant was then concentrated by lyophilization or ultrafiltration prior to radioimmunoassay and immunoblotting.

2. Detection of the HBsAg Gene Construct

The stable integration of the HBsAg construct (expression vector) for plant cell transfection was tested by hybridization assays of genomic DNA digested with Eco R1, and with a combined mixture of Bam H1 and Sst 1 in each plant tissue for both control and HBsAg-transfected plants with a HBsAg coding sequence probe using standard southern blots[60]. In addition, seeds were collected from self-fertilized plants, and progeny were analyzed by standard Southern analysis.

E. Regeneration of HBsAg Transgenic Tomato Plants

Once the transgenic plant has been perfected, the transgenic plant is regenerated by growing multiples of the transgenic plant to produce the oral vaccine. Of course, the most common method of plant propagation is by seed. Regeneration by seed propagation, however, has the deficiency that there is a lack of uniformity in the crop. Seeds are produced by plants according to the genetic variances governed by Mendelian rules. Basically, each seed is genetically different and each will grow with its own specific traits. Therefore, it is preferred that the transgenic plant be produced by homozygous selection such that the regenerated plant has the identical traits and characteristics of the parent transgenic plant, e.g. a reproduction of the vaccine.

F. Administration of HBsAg Vaccine to Humans Through Consumption of Tomato Juice Produced from HBsAg Transgenic Tomatoes Once the vaccine is produced through the mass regeneration of the transgenic plant, the crop is harvested and utilized directly as food or processed into a consumable food. Although the food may be processed as a solid or liquid, in some cases it is preferred that it be in liquid form for ease of consumption. The transgenic tomatoes could be homogenized to produce tomato juice which could be bottled for drinking. HBsAg vaccine administration is accomplished by a human drinking the tomato juice or consuming the fruit in a quantity and time scale (once or multiple doses over a period of time) to confer immunity to hepatitis B virus infection.

EXAMPLE II

A.1 Construction of Hepatitis B Surface Antigen Expression Vector pHB101

Figure 3:
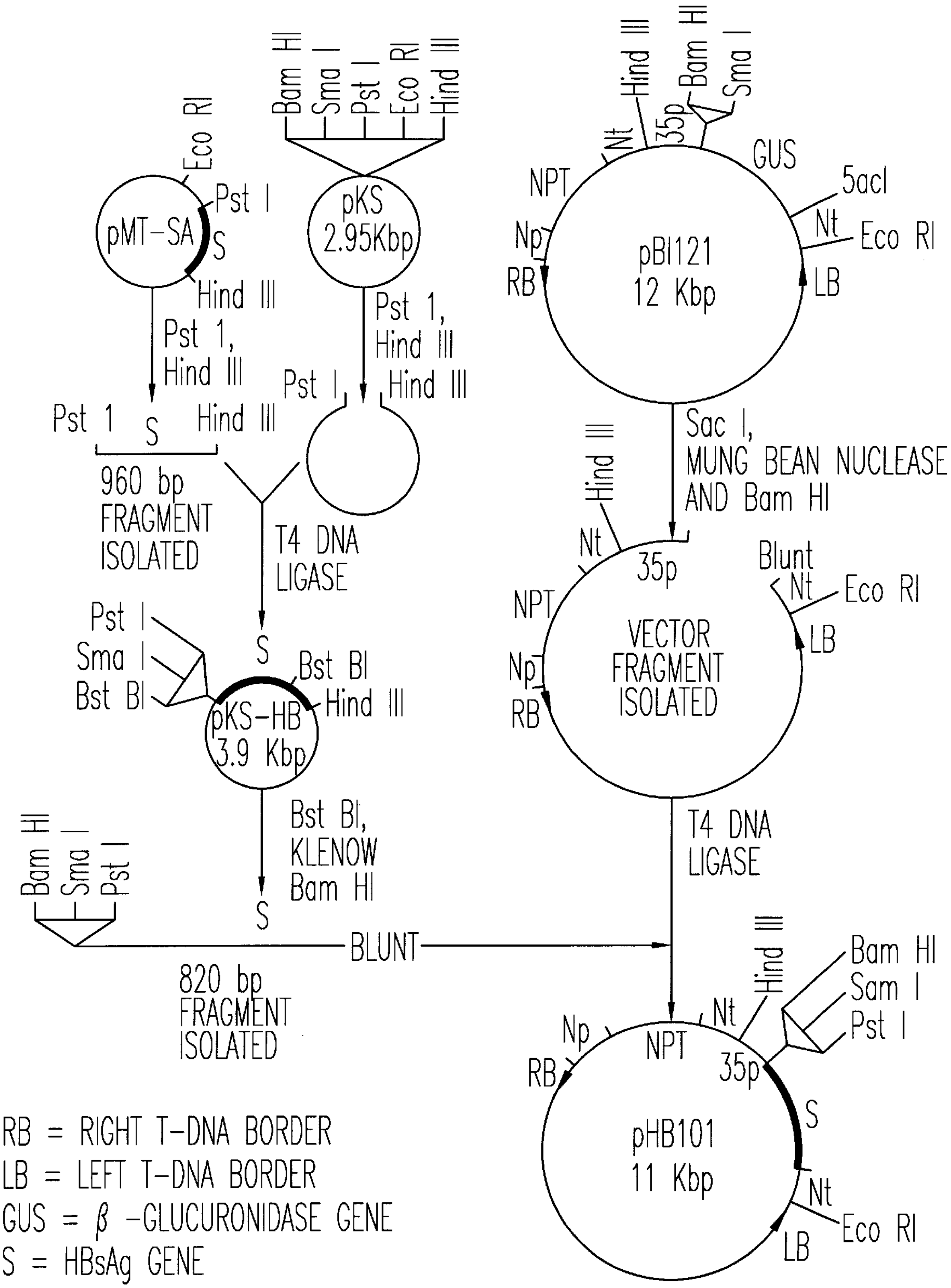
FIG. 3 is a diagrammatic plasmid construct illustrating the construction of the plasmid vector pHB101 containing the HBsAg gene for producing the HBsAg antigen in a plant.

Referring to the plasmid construct illustrated in FIG. 3, the DNA sequence encoding for HBsAg contained within restriction endonuclease sites Pst I-Hind III on plasmid pMT-SA (provided by Li-he Guo, Chinese Academy of Sciences) was excised and subsequently ligated into the unique Bam HI-Sac I site of the excised beta-Glucuronidase (GUS) gene on plasmid pBI121 to construct the binary plasmid pHB101.

Plasmid pBI121, obtained from Clonetech Laboratories, Inc., Palo Alto, Calif., has cleavage sites for the restriction endonucleases Bam HI and Sac I located between the CaMV 35S promoter and the GUS structural gene initiation sequence and between the GUS gene termination sequence and the NOS polyadenylation signals, respectively. Plasmid pBI121 was selected since the GUS structural gene can be excised from the plasmid using Bam HI and Sac I, another structural gene encoding an antigenic protein can be inserted, and the new gene will be functionally active in plant gene expression. Plasmid pBI121 also contains a NPT II gene encoding neomycin phosphotransferase II and conferring kanamycin resistance. The NPT II gene is flanked by promoter and polyadenylation sequences from a Nopaline synthase (NOS) gene. The HBsAg DNA coding sequence[64,65] (the S gene) was excised from plasmid pMT-SA (constructed at Chinese Academy of Sciences) as a Pst I-Hind III fragment and isolated by electrophoresis in a one percent (1%) agarose gel. The Pst-Hind III fragment was visualized in the agarose gel by staining with ethidium bromide, illuminated with ultraviolet light (UV) and purified with a Prep-a-Gene kit (BioRad Laboratories, Richmond, Calif.). The HBsAg coding region on the Pst I-Hind III fragment was then ligated into the Pst I-Hind III digested plasmid pBluescript KS (Stratagene, La Jolla, Calif.) to form the plasmid pKS-HBS. The HBsAg gene in plasmid pKS-HBS was then opened 116 base pairs (bp) 3' to the termination codon with BstBI and the resulting ends were blunted by filling with Klenow enzyme and dCTP/dGTP. The entire coding region (820 bp) was then excised with Bam HI, which is site derived from the plasmid vector pBluescript. This results in the addition of Barn HI and Sma I sites 5' to the original HBsAg coding sequence from plasmid pMT-SA.

Plasmid pBI121[66], obtained from Clonetech, Laboratories, Inc., Palo Alto, Calif., was digested with Sac I and the ends blunted with mung bean nuclease. The GUS coding region was then released from pBI121 by treatment with Bam HI and the 11 kilobase pair (kbp) GUS-less pBI121 plasmid vector isolated. Subsequently, the HBsAg coding fragment excised from pKS-HB was ligated into the GUS-less plasmid pBI121 to yield plasmid pHB101 (FIG. 3). Transcription of the HBsAg gene in this construct is driven by the cauliflower mosaic virus 35S (CaMV 35S) promoter derived from pBI121, and the polyadenylation signal is provided by the nopaline synthase terminator.

Figure 5:
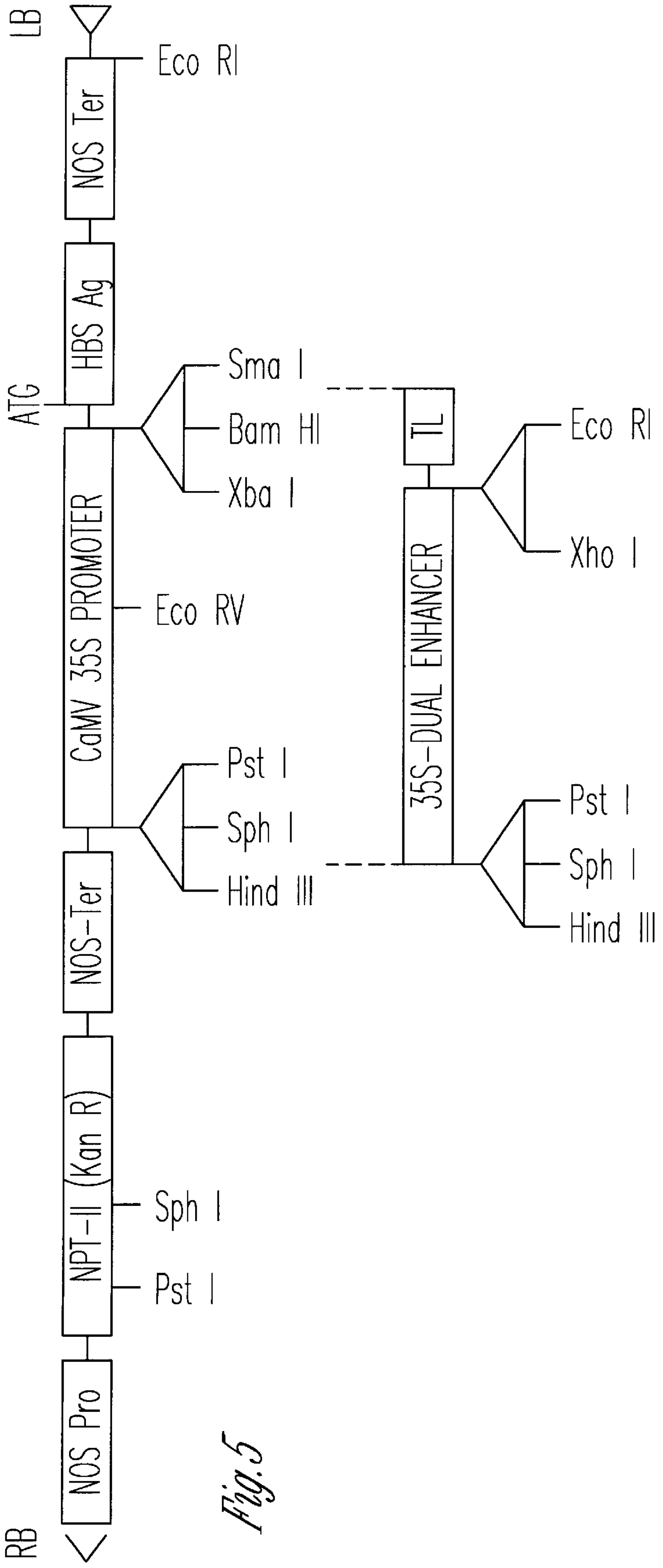
FIG. 5 is a map of the coding sequence for three structural genes and their regulatory elements in the plasmids pHB101 and pHB102.

The plasmid vector pHB101 then contains 1) a neomycin phosphotransferase II (NPTII) gene which provides the selectable marker for kanamycin resistance; 2) a HBsAg gene regulated by a cauliflower mosaic virus (CaMV 35S) promoter sequence; and 3) right and left T-DNA border sequences which effectively cause the DNA sequences for the NOS and HBsAg genes to be transferred to plant cells and integrated into the plant genome. The diagrammatic structure of pHB101 is shown in FIG. 5.

A.2 Construction of Hepatitis B Surface Antigen Expression Vector pHB102

Plasmid pHB102, an improved expression vector, was constructed from plasmid pHB101 by removal of the CaMV 35S promoter and insertion of a modified 35S promoter linked to a translational enhancer element. The CaMV 35S promoter in the plasmid pRTL2-GUS[67] contains a duplication of the upstream regulatory sequences between nucleotides −340 and −90 relative to the transcription initiation site. Fused to the 3' end of the promoter is the tobacco etch virus 5' nontranslated leader sequence (TL), which acts as a translational enhancer in tobacco cells.

Figure 4:
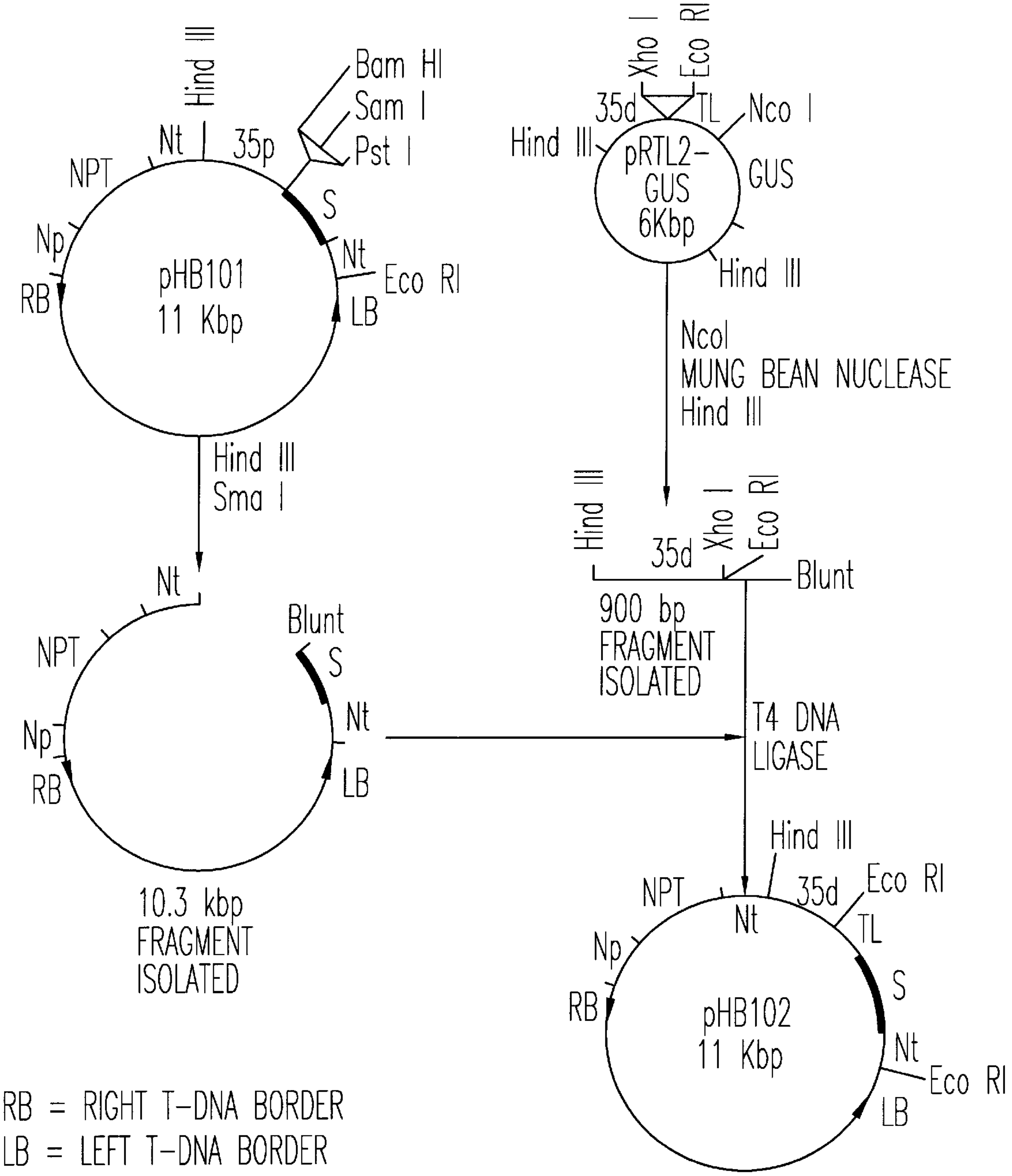
FIG. 4 is a diagrammatic plasmid construct illustrating the construction of the plasmid vector pHB102 containing the HBsAg gene for producing the HBsAg antigen in a plant.

As seen in FIG. 4, the promoter (with dual enhancer) was obtained from plasmid pRTL2-GUS. pRTL2-GUS was digested with Nco I and the ends were blunted with mung bean nuclease. The CaMV 35S with duplicated enhancer linked to tobacco etch virus (TEV) 5' nontranslated leader sequence (the promoter-leader fragment) was then released by digestion with Hind III, and purified by agarose gel electrophoresis. Plasmid pHB101 was digested with Hind III and Sma I to release the CaMV 35S promoter fragment and the promoter-less plasmid vector was purified by agarose gel electrophoresis. This yielded a blunt end just 5' to the HbsAg coding sequence for fusion with the blunted Nco I site at the 3' end of the purified promoter-leader fragment from pRTL2-GUS. Then the promoter-leader fragment from pRTL2-GUS was ligated into the Hind III-Sma I site on promoter-less plasmid pHB101 to yield plasmid pHB102.

The HBsAg coding region of plasmid pHB102 lies upstream of the nopaline synthase (NOS) terminator. The plasmid contains the left and right borders of the T-DNA that is integrated into the plant genomic DNA via *Agrobacterium tumefaciens* mediated transformation, as well as the neomycin phosphotransferase (NPT II) gene which allows selection with kanamycin. Expression of the HbsAg gene is driven by the CaMV 35S with dual transcriptional enhancer linked to the TEV 5' nontranslated leader. The TEV leader acts as a translational enhancer to increase the amount of protein made using a given amount of template mRNA.[67]

B. Transfer of Binary Vectors, pHB101 and pHB102, to *A. tumefaciens*

Plasmid pHB101, containing the HbsAg gene and the CaMV 35S promoter, and plasmid pHB102, containing the HBsAg gene and CaMV 35S promoter with dual transcription enhancer linked to the TEV 5' nontranslated leader were then separately transferred to *Agrobacterium tumefaciens.*

Plasmid pHB101 or pHB102, each containing the HBsAg gene, was transferred to the *A. tumefaciens* strain LBA4404 obtained from Clonetech Laboratories, Inc. as in Example I.

*A. tumefaciens* was cultured in 50 milliliters (50 ml) of YEP (yeast extract-peptone broth)[58] containing two-tenths milligrams per milliliter (0.2 mg/ml) streptomycin until the optical density (O.D.) at 600 nanometers (nm) of the culture reaches about five tenths (0.5). The cells were then centrifuged at 2000 times gravity (2000XG) to obtain a bacterial cell pellet. The Agobacterium pellet was resuspended in ten milliliters of ice cold one hundred fifty millimolar sodium chloride (150 mM $NaCl_2$). The cells were then centrifuged again at 2000XG and the resulting Agrobacterium pellet was resuspended in one milliliter (1 ml) of ice cold twenty millimolar calcium chloride (20 mM $CaCl_2$). Five-tenths microgram (0.5 $\mu$g) of plasmid pHB101 or plasmid pHB102 was added to two tenths milliliters (0.2 ml) of the calcium chloride suspension of *A. tumefaciens* cells in a one and five tenths milliliter (1.5 ml) microcentrifuge tube and incubated on ice for sixty minutes. The plasmid pHB101 or pHB102 DNA and *A. tumefaciens* cells mixture was frozen in liquid nitrogen for one minute, thawed in a twenty-eight degree Celsius (28° C.) water bath, and then mixed with five volumes or 1 milliliter (1 ml) of YEP (yeast extract-peptone broth). The plasmid pHB101 or pHB102 and *A. tumefaciens* mixture was then incubated at twenty-eight degrees Celsius (28° C.) for four hours with gende shaking. The mixture was plated on YEP (yeast extract-peptone broth) agar medium containing fifty micrograms per milliliter (50 $\mu$g/ml) kanamycin. Optimum drug concentration may differ depending upon the Agrobacterium strain in other experiments. The plates were incubated for three days at twenty-eight degrees Celsius (28° C.) before selection of resultant colonies which contained the transformed Agrobacterium harboring the pHB101 or the pHB102 plasmids. These colonies were then transferred to five millileters (5 ml) of YEP (yeast extract-peptone broth) containing fifty micrograms per milliliter (50 $\mu$g/ml) of kanamycin for three days at twenty-eight degrees Celsius (28° C.).

The presence of pHB101 or pHB102 DNA in the transformed Agrobacterium culture was verified by restriction mapping of the plasmid DNA purified by alkaline lysis of the bacterial cells.[59]

C. Plant Transformation by *A. tumefaciens* containing the HBsAg Gene as Part of the Ti Vector System Tobacco plants were transformed by the leaf disc method utilizing *Agrobacterium tumefaciens* containing either plasmid pHB101 or pHB102 and then the kanamycin resistant transformed tobacco plants were regenerated.

Leaf disc transformation was performed in accordance with the procedure of Horsch et al[6]. Tobacco seeds (*Nicotiana tabacum L. cv Samsun*) were surface sterilized with twenty per cent (20%) household bleach (diluted one to five from the bottle) for ten minutes and then washed five times with sterile water. The seeds were sown on sterile MSO[6] medium in GA-7 boxes (Magenta Corporation, Chicago Ill.). The seedlings were grown under moderate light for four to six weeks, and leaf tissue was excised with a sterile scalpel and cut into five-tenths square centimeter (0.5 $cm^2$) pieces.

The *A. tumefaciens* containing pHB101 or pHB102 which had been grown in YEP (yeast extract-peptone broth) medium were diluted one to ten with MSO[6] for tobacco leaf pieces. Leaf pieces were inoculated by immersion in the diluted transformed *A. tumefaciens* culture and cocultured on regeneration medium MS 104[6] for two days at twenty-seven degrees Celsius (27° C.). Leaf pieces were then washed with sterile water to remove the free *A. tumefaciens* cells and placed on fresh MS selection medium which contained two hundred micrograms per milliliter (200 $\mu$g/ml) kanamycin to select for transformed plant cells and two hundred micrograms per milliliter (200 $\mu$g/ml) cefotaxime to inhibit bacterial growth. Leaf pieces were subcultured every two weeks on fresh MS selection medium until shoots appeared at the cut edges. As shoots formed at the edge of the leaf pieces and grew large enough for manual manipulation, they were excised (usually at three to six weeks after cocultivation with transformed *A. tumefaciens*) and transferred to a root-inducing medium, e.g. MS rooting medium containing one hundred micrograms per milliliter of kanamycin (100 $\mu$g/ml). As roots appeared, the plantlets were either allowed to continue to grow under sterile tissue culture conditions or transferred to soil and allowed to grow in a controlled environment chamber.

D. Analysis of RNA from Transformed Tobacco

The regenerated kanamycin-resistant pHB101 and pHB102 transformed tobacco plants were analyzed by hybridizing RNA samples with a $^{32}P$ labelled probe encompassing the HBsAg gene coding region.

Total RNA from the leaves of the p HB101 transformed tobacco plants was isolated as described[68]. Approximately four tenths of a gram (0.4 g) of young growing leaf tissue from a transformed plant was frozen in liquid nitrogen and ground to a powder with a cold mortar and pestle. The powder was resuspended in five milliliters (5 ml) of RNA extraction buffer composed of two hundred millimolar (0.2M) Tris-HCl, pH 8.6; two hundred millimolar sodium chloride (0.2M NaCl); twenty millimolar ethylenediaminetetraacetic acid (20 mM EDTA) and two percent sodium dodecyl sulfate (2% SDS) and immediately extracted with five milliliters (5 ml) of phenol saturated with ten millimolar (10 mM) Tris-HCl, pH 8.0 per one millimole ethylenediaminetetraacetic acid (1 mM EDTA), and five milliliters (5 ml) of chloroform. After centrifugation at three thousand times gravity (3,000XG) to separate the phases, the upper aqueous layer was removed and made to three tenths molar (0.3M) potassium acetate, pH 5.2. The nucleic acids in the extract were precipitated with two and a half (2.5) volumes of ethanol, pelleted at eight thousand times gravity (8000XG), dried under reduced pressure, resuspended in one milliliter (1 ml) of water, and reprecipitated with the addition of one milliliter (1 ml) of six molar (6M) ammonium acetate and five milliliters (5 ml) of ethanol. The final pellet was dried and resuspended in two tenths of a milliliter (0.2 ml) of water, and the concentration of RNA estimated by measuring the absorbance of the samples at 260 nanometers (nm), assuming that a solution of one milligram per milliliter (1 mg/ml) RNA has an absorbance of twenty-five (25) units.

Five micrograms of each RNA sample was denatured by incubation for fifteen minutes at sixty-five degrees Celsius (65° C.) in twenty millimolar (20 mM) MOPS (3-N-morpholino) propanesulfuric acid, pH 7.0; ten millimolar (10 mM) sodium acetate; one millimolar ethylenediaminetetraacetic acid (1 mM EDTA); six and one half percent (6.5% w/v) formaldehyde; fifty percent (50% v/v) formamide, and then fractionated by electrophoresis in one percent (1%) agarose gels. The nucleic acids were transferred to a nylon membrane by capillary blotting[59] for sixteen hours in twenty-five millimolar (25 mM) sodium phosphate, pH 6.5. Then the nucleic acids were crosslinked to the membrane by irradiation with ultraviolet (UV) light and the membrane pretreated with hybridization buffer [twenty-five hundredths molar (0.25M) sodium phosphate, pH 7.0; one millimolar ethylene diamine tetraacetic acid (1 mM EDTA); seven percent (7%) sodium dodecyl sulfate (SDS)] for one hour at sixty-eight degrees Celsius (68° C.). The membrane was probed with $10^6$ counts per minute per milliliter (cpm/ml) $^{32}$P-labelled random-primed DNA using a 700 base pair (bp) Bam HI-Acc I fragment from plasmid pKS-HBS which includes most of the coding region for HBsAg. Blots were hybridized at sixty-eight degrees Celsius (68° C.) in hybridization buffer and washed twice for five hundred and fifteen minutes with forty millimolar (40 mM) sodium phosphate, pH 7.0 per one millimolar ethylene diaminetetraacetic acid (1 mM EDTA) per five percent sodium dodecyl sulfate (5% SDS) at sixty-eight degrees Celsius (68° C.) and exposed to X-OMAT AR film for twenty hours.

Figure 6A:
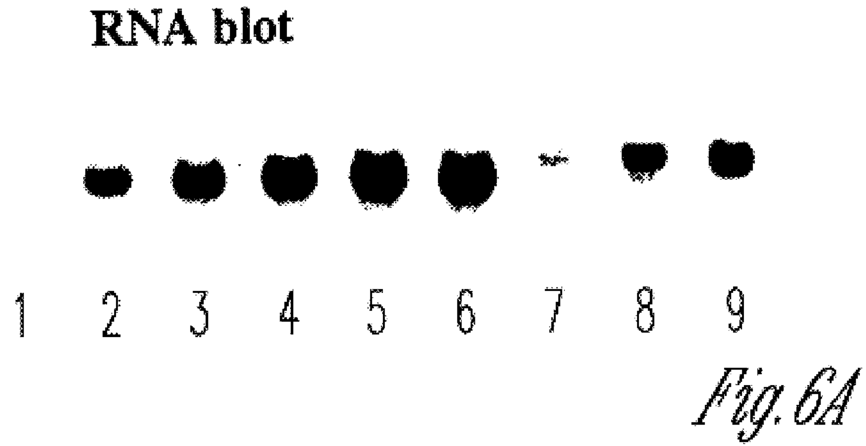
FIG. 6A indicates the HBsAg mRNA levels in transgenic tobacco plants.

The results of the RNA hybridization probe with selected transformants harboring the plasmid pHB101 construct and with a wild-type control (wt) can be seen in FIG. 6A. The signals were highly variable between transformants, as expected due to the effects of position of insertion into the genomic DNA and differing copy number. The transcripts were about 1.2 kb in length by comparison with the RNA standards, which was consistent with the expected size. The wild-type control leaf RNA showed no detectable signal at this stringency of hybridization. Substantial steady-state levels of mRNA which specifically hybridized with the HBsAg probe was present in the leaves of selected transformants which indicated that mRNA stability was not a problem for the expression of HBsAg in tobacco leaves.

E. Analysis of Protein from Transformed Tobacco Plants

Figure 6B:
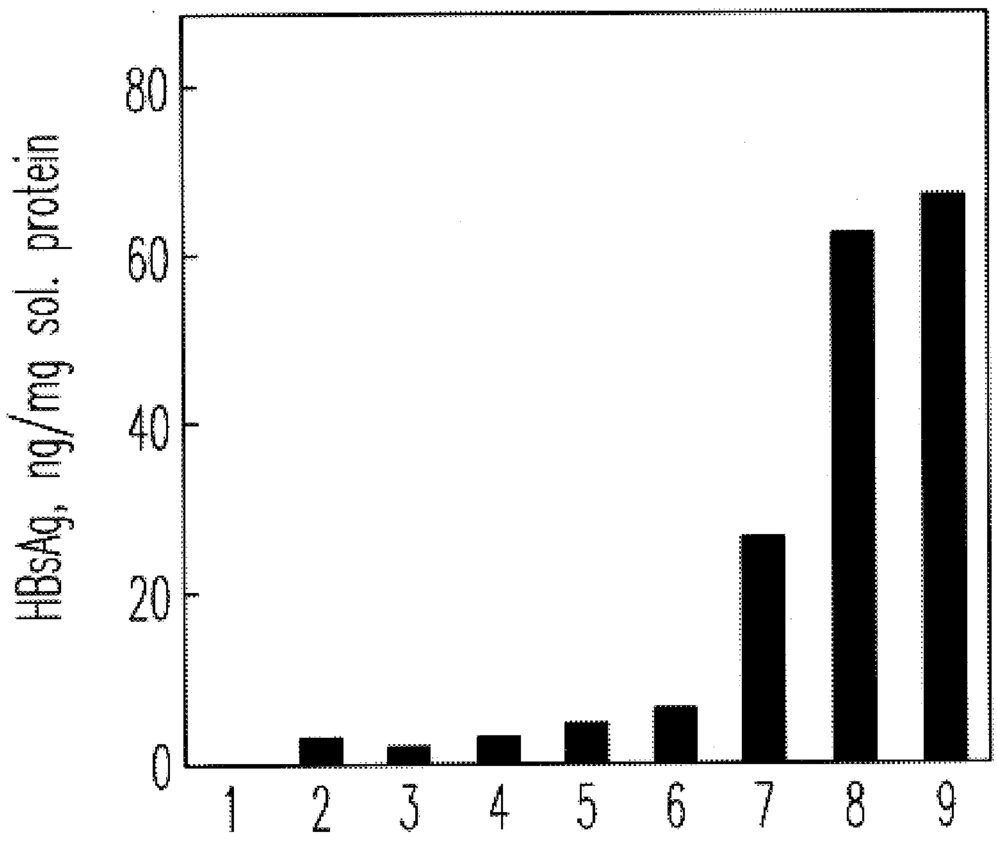
FIG. 6B indicates the HBsAg protein levels in transgenic tobacco plants.

Protein was extracted from transformed tobacco leaf tissues by homogenization with a Ten-Broek ground glass homogenizer (clearance 0.15 mm) in five volumes of buffer containing twenty millimolar (20 mM) sodium phosphate, pH 7.0, one hundred fifty millimolar (150 mM) sodium chloride, twenty millimolar (20 mM) sodium ascorbate, one-tenth percent (0.1 %) Triton X-100, and five tenths millimolar (0.5 mM) PMSF, at four degrees Celsius (4° C.). The homogenate was centrifuged at one thousand times gravity (1000XG) for five minutes and the supernatant centrifuged at twenty-seven thousand times gravity (27,000XG) for fifteen minutes. The 27,000XG supernatant was then centrifuged at one hundred thousand times gravity (100,000XG) for one hour and the pellet resuspended in extraction buffer. The protein in the different fractions was measured by the Coomassie dye-binding assay (Bio-Rad). HBsAg protein was assayed by the AUSZYME Monoclonal kit (Abbott Laboratories, Abbott Park, Ill.) using the positive control, HBsAg derived from human serum, as the standard. The positive control was diluted to give HBsAg protein levels of nine hundredths to one and eight tenths nanograms (0.09–1.8 ng) per assay. After color development, the absorbance at four hundred ninety-two nanometers (492 nm) was read and a linear relationship was found. As seen in FIG. 6B, the weld-type control plant contained no detectable HBsAg protein (Column 1); fairly low levels of HBsAg protein were observed, ranging from three to ten nanograms per milligram (3–10 ng/mg) soluble protein for the pHB101 construct (Columns 2 through 6); and from twenty-five to sixty-five nanograms per milligram (25–65 ng/mg) for the pHB102 construct (Columns 7 through 9). The reaction was specific because the wild-type tobacco showed no detectable HBsAg protein. HBsAg from human serum and recombinant HBsAg (rHBsAg) from plasmid-transformed yeast occur as approximately twenty nanometer (20 nm) spherical particles consisting of protein embedded in a phospholipid bilayer. Ninety-five percent of the rHBsAg in the 27,000XG supernatants of transgenic tobacco leaf extracts pelleted at 2000,000XG for thirty minutes. This suggested a particle form. Thus, evidence was sought to ascertain if rHBsAg in tobacco existed as particles.

F. Immunoaffinity Purification of HBsAg from Transformed Tobacco Plants

Transformed tobacco leaf extracts were tested for the presence of material which reacts specifically with monoclonal antibody to serumderived HBsAg. Further tests were conducted to determine if the recombinant HBsAg material in the transformed tobacco leaves was present as particles and the size range of the particles.

Figure 7A:
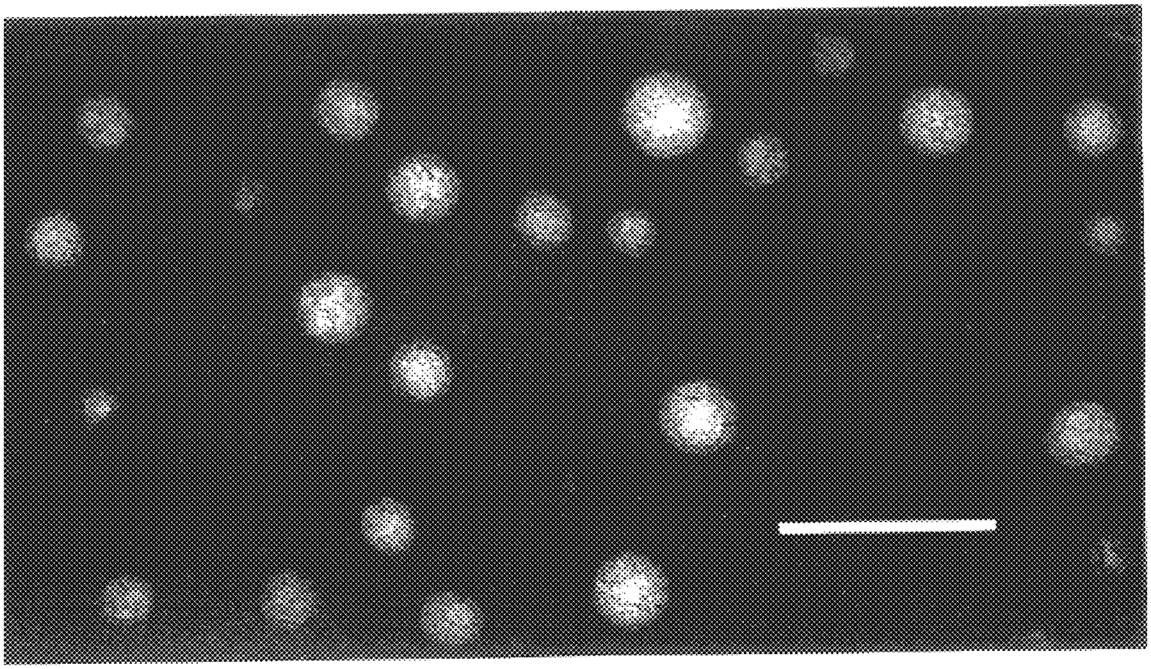
FIG. 7 is a micrograph of immunoaffinity purified rHBsAg with a corresponding histogram.
Figure 7B:
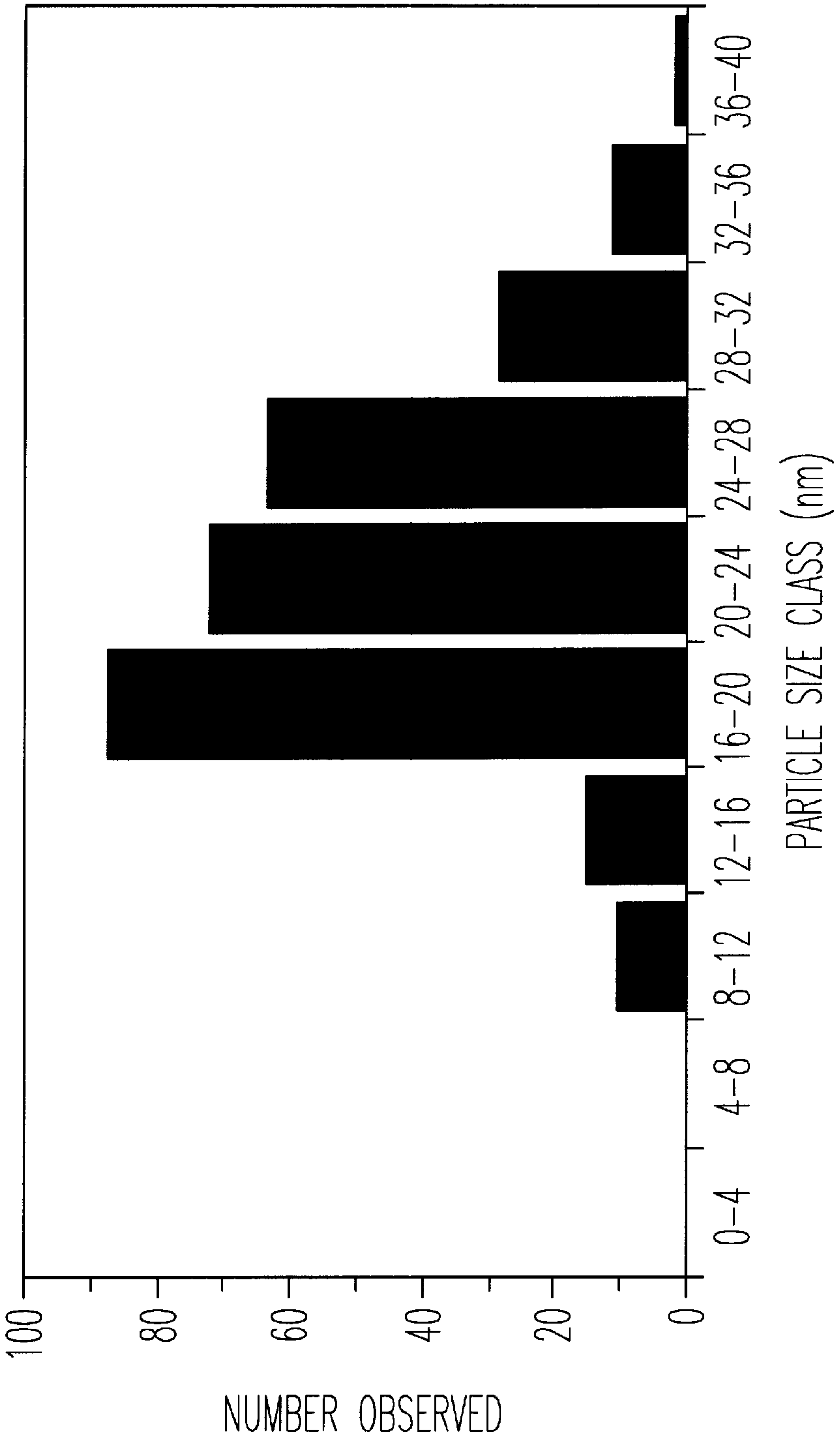

Monoclonal antibody against HBsAg, clone ZMHB1, was obtained from Zymed Laboratories (South San Francisco, Calif.). The immunogen source for this antibody is human serum. The monoclonal antibody was bound to Affi-Gel HZ hydrazide gel (Bio-Rad Laboratories, Richmond, Calif.) according to the instruction supplied in the kit. The 100,000XG resuspended soluble material was made to five tenths molar (0.5M) sodium chloride and mixed with the immobilized antibody-gel by end-over-end mixing for sixteen hours at four degrees Celsius (4° C.). The gel was washed with ten volumes of PBS.5 [ten millimolar (10 mM) sodium phosphate, pH 7.0, five tenths molar (0.5M) sodium chloride] and ten volumes of PBS. 15 [fifteen hundredths molar (0.15M) sodium chloride] and bound HBsAg eluted with two tenths molar (0.2M) glycine, pH 2.5. The eluate was immediately neutralized with Tris-base, and particles pelleted at one hundred and nine thousand times gravity (109,000XG) for one and a half hours at five degrees Celsius (5° C.). The pelleted material was negatively stained with phosphotungstic acid and visualized with transmission electron microscopy using a Phillips CMIO microscope. The presence of rHBsAg particles were revealed by negative staining and electron microscopy, FIG. 7. rHBsAg particles ranged in diameter between ten and forty nanometers (10–40 nm). Most particles were between sixteen and twenty-eight nanometers (16–28 nm). These are very similar to the particles observed in human serum,[69] although no rods were observed. The rHBsAg particles from yeast occur in a range of sizes with a mean of seventeen nanometers (17 nm).[2] Thus rHBsAg produced in transgenic tobacco leaves has a similar physical form to the human HBsAg.

G. Sucrose and Cesium Chloride Gradient Analysis of HBsAg from Transgenic Tobacco Further evidence of the particle behavior of rHBsAg was obtained from sedimentation and buoyant density studies of the transgenic tobacco leaf extracts.

Extracts of the transgenic tobacco leaf tissue were made as described in the protein analysis section and five tenths milliliter (0.5 ml) of the 27,000XG supernatants were layered on linear eleven milliliter (11 ml) five to thirty percent (5–30%) sucrose gradients made in ten millimolar (10 mM) sodium phosphate, pH 7.0, fifteen hundredths molar (0.15M sodium chloride or discontinuous twelve milliliters (12 ml) one and one tenth to one and four tenth grams per milliliter (1.1–1.4 g/ml) cesium chloride gradients made in ten millimolar (10 mM) sodium phosphate, pH 7.0 [three milliliters (3 ml) each of one and one tenth, one and two tenths, one and three tenths, and one and four tenths grams per milliliter (1.1, 1.2, 1.3 and 1.4 g/ml) cesium chloride]. Positive control HBsAg from the AUSZYME kit was also layered on separate gradients. The sucrose gradients were centrifuged in a Beckman SW41Ti rotor at thirty-three thousand revolutions per minute (33,000 rpm) for five hours at five degrees Celsius (5° C.), and fractionated into one milliliter (1 ml) fractions while monitoring the absorbance at two hundred and eighty nanometers (280 nm). The cesium chloride gradients were centrifuged in a Beckman SW40Ti rotor at thirty thousand revolutions per minute (30,000 rpm) for twenty five hours at five degrees Celsius (5° C.), and fractionated into five tenths milliliter (0.5 ml) fractions. HBsAg in the gradient was assayed using the AUSZYME kit as described above.

Figure 8:
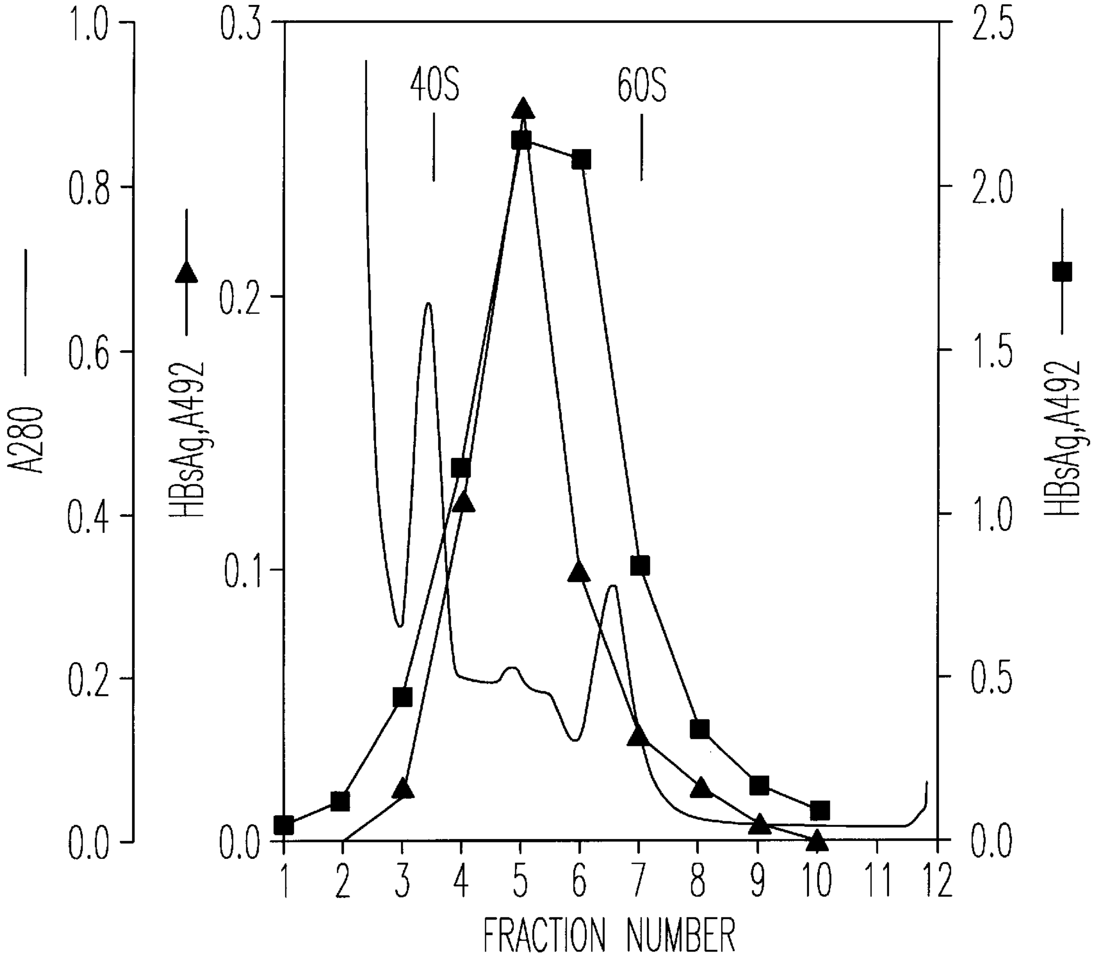
FIG. 8 is a sucrose density gradient sedimentation of HBsAg from transgenic tobacco.

FIG. 8 shows a sucrose gradient profile of rHBsAg activity from the transgenic tobacco leaves harboring the plasmid construct pHB102. The transgenic tobacco rHBsAg sedimented with a peak near the 60S ribosomal subunit, and the serum-derived HBsAg material sedimented in a somewhat sharper peak just slightly slower. This data is consistent with the finding that human HBsAg sediments at 55S.[70] The observation that the plant rHBsAg material sedimented slightly faster and with a broader peak than the human HBsAg is consistent with the larger mean size of the rHBsAg plant particles and the wider range of particle sizes.

Figure 9:
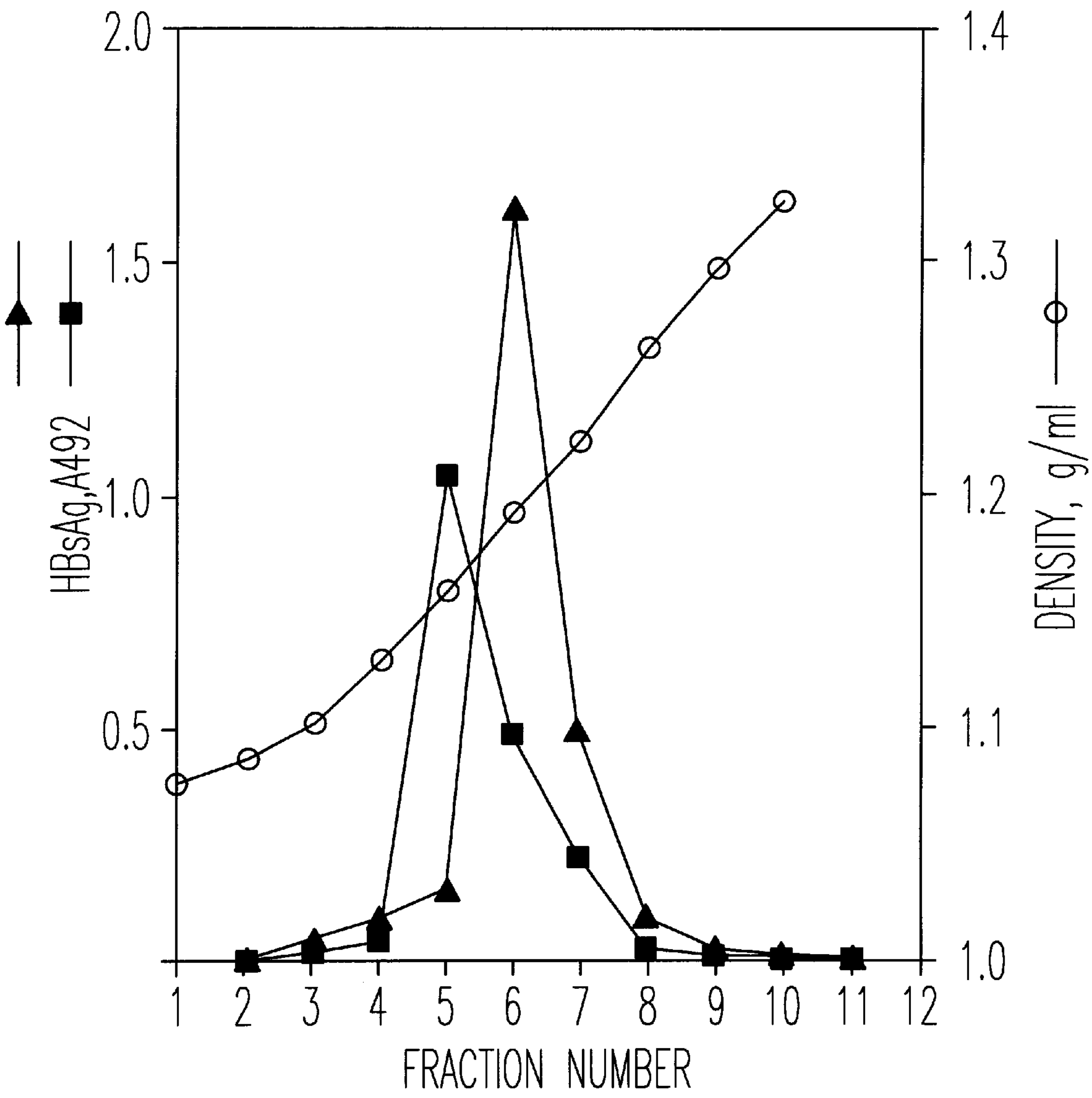
FIG. 9 is a buoyant density gradient sedimentation of HBsAg from transgenic tobacco.

The buoyant density of the rHBsAg particles from transgenic tobacco plants in cesium chloride, FIG. 9, was found to be approximately one and sixteen hundredths grams per milliliter (1.16 g/ml), while the human HBsAg particles showed a density of about one and two tenths grams per milliliter (1.20 g/ml). Thus, the rHBsAg from the transgenic tobacco plants exhibits sedimentation and density properties that are very similar to the subviral HBsAg particles obtained from human serum. Most importantly, HBsAg in the particle form is much more immunogenic than that found in the peptide form alone.[2]

H. Reproduction of HBsAg Transgenic Tobacco Plants

Reproduction of transgenic plants was accomplished as stated in Example I.

EXAMPLE III

A. Transformation of Tomato with HBsAg Gene

Tomato, *Lycopersicom esculentum* var. VFN8, was transformed as in Example II. B and C by the leaf disc method using *Agrobacterium tumefaciens* strain LBA4404 as a vector, McCormick et al., 1986.[23] *A. tumefaciens* cells harboring plasmid pHB102, constructed as in Example II. A.2, which carries the HBsAg coding region fused to the tobacco etch virus untranslated leader, Carrington & Freed, 1990,[73] and the cauliflower mosaic virus 35S promoter, were used to infect cotyledon explants from seven day old seedlings. The explants were not preconditioned on feeder plates, but infected directly upon cutting, and cocultivated in the absence of selection for two days. Explants were then transferred to medium B, McCormick et al., 1986,[23] containing five-tenths milligrams per millilter (0.5 mg/ml) carbenicillin and one-tenth milligram per milliliter (0.1 mg/ml) kanamycin for selection of transformed callus. Shoots were rooted in MS medium containing one-tenth milligram per milliliter (0.1 mg/ml) kanamycin but lacking hormones, and transplanted to soil and grown in a greenhouse.

Several independent kanamycin-resistant callus lines were obtained after Agrobacterium-mediated transformation of the tomato variety VFN8. One of these lines regenerated shoots with high frequency and was rooted and grown in soil in the greenhouse. The tissues from these plants were used for the protein and RNA analyses.

B. Quantitation of BsAg in Leaves and Fruits

Plants tissues were extracted by grinding in a mortar and pestle with solid carbon dioxide ($CO_2$), and suspended in three volumes of buffer containing twenty millimolar (20 mM) sodium phosphate, one hundred fifty millimolar sodium chloride (150 mM NaCl), five tenths millimolar phenylmethylsulfonyl fluoride (0.5 mM PMSF), one tenth percent (0.1%) Triton X-100, pH 7.0. After centrifuging the homogenate at ten thousands times gravity (10,000 xg) for five minutes at four degrees Celsius (4° C.), aliquots of the supernatant were assayed for total soluble protein by the method of Bradford[74] and for HBsAg with the Auszyme II kit (Abbott Laboratories) as described in Example II. E.

HBsAg Levels in Transformed Tomato Tissues

In order to test for accumulation of HBsAg protein in transgenic plants, extracts of leaf and fruit were made, which were used for HBsAg-specific ELISA. A standard curve was obtained using authentic HBsAg which was derived from the serum of infected individuals. Table 1 shows the levels of accumulation of HBsAg in leaves and ripe fruit of transgenic plants. Young leaf and red fruit from greenhouse-grown transgenic tomato plants were extracted and assayed for total soluble protein and HBsAg as described above. Similar tissues from untransformed control tomato plants showed very low background for HBsAg.

The level found in tomato leaves is similar to the highest level found in leaves of transgenic tobacco by Mason et al., 1992[72], and represents 0.007% of the total soluble protein. The amount of HBsAg in ripe fruit was somewhat lower, 0.0043%, or 87 ng/g fresh weight. Similar extracts of untransformed tomato leaves showed negligible amounts of anti-HBsAg reactive material, at least 50-fold lower than the transformed plants.

The level of expression in the tomato fruit, although somewhat lower on a total protein basis, represents a substantial proportion of the whole plant accumulation of HBsAg because the fruit are much more dense than the leaves. A small tomato weighing one hundred grams would contain approximately nine micrograms (9 $\mu$g) of HBsAg.

TABLE 1

HBSAg Levels in Transgenic Tomato Leaf and Fruit

| Organ | ng/mg total soluble protein (%) | ng/g fresh weight |
|---|---|---|
| Leaf | 70 (0.007%) | |
| Fruit (red) | 43 (0.0043%) | 87 |

C. RNA Extraction and Northern Blotting

RNA was extracted as described in Example II. D., except that the tissues were ground with solid carbon dioxide ($CO_2$) instead of liquid nitrogen ($N_2$). RNA was fractionated and blotted to nylon membranes (Boehringer-Mannheim), fixed by irradiation on a ultraviolet transilluminator for three minutes, and air dried. Total RNA on the blot was visualized by staining with twenty-five hundredths percent (0.25%) methylene blue per twenty-five hundredths molar sodium acetate (0.25 M NaOAc), pH 4.5 for five minutes and destaining with water. The blot was then prehybridized in twenty-five hundredths molar (0.25 M) sodium phosphate, pH 7.0, ten millimolar ethylenediaminetetraacetic acid (10 mM EDTA), seven percent sodium dodecyl sulfate (7% SDS) for one hour at sixty-eight degrees Celsius (68° C.) and probed with digoxygenin-labeled random-primed DNA made using the HBsAg coding region as template according to the manufacturer's instructions (Genius 2 Kit, Boehringer-Mannheim). After washing the blot twice with forty millimolar (40 mM) sodium phosphate, pH 7.0, five percent sodium dodecyl sulfate (5% SDS) at sixty-eight degrees Celsius (68° C.) and twice with forty millimolar (40 mM) sodium phosphate, pH 7.0, one percent sodium dodecyl sulfate (1% SDS) at sixth-eight degrees Celsius (68° C.), the hybridized RNA was detected by probing with anti-digoxygenin-alkaline phosphatase conjugate and developing color for sixteen hours according to the manufacturer's instructions (Genius 2 Kit, Boehringer-Mannheim).

Figure 10A:
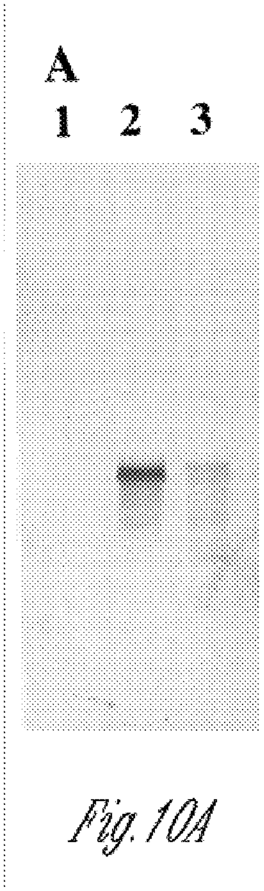
FIG. 10 is an RNA blot of transformed tomato leaf.
Figure 10B:
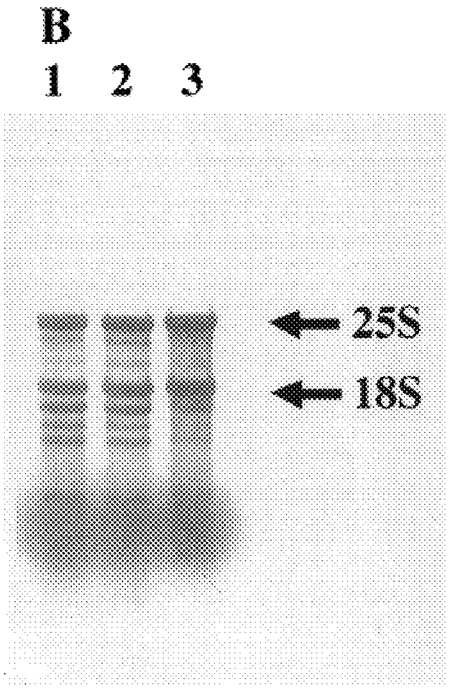

The activity of the HBsAg gene in transgenic plants was assessed by RNA blotting. Total RNA isolated from transformed tomato leaves and green fruit and from untransformed leaves was fractionated in a denaturing agarose gel, transferred to a nylon membrane, and hybridized with random-primed digoxygenin-labeled probe made using the HBsAg coding sequence as template. FIG. 10A shows that RNA from transformed tomato leaf and fruit hybridized with the HBsAg probe, while RNA from untransformed leaf showed no detectable signal. The level of HBsAg mRNA in leaves was approximately three to five times greater than in fruit, on a total RNA basis. FIG. 10B shows a similar RNA blot stained with methylene blue to reveal the total RNA pattern, and indicates that the samples were loaded with equivalent amounts of total RNA. Thus, the HBsAg transgene is transcribed faithfully in transgenic tomato leaf and fruit, and accumulates to substantial levels. The yield of RNA from ripe fruit was poor, and was not analyzed by RNA blotting.

D. Tissue Blotting for HBsAg Detection

Leaves of transformed or untransformed tomato plants were excised and pressed on fine-grain sandpaper before blotting abaxial side down on nitrocellulose. Tomato fruits were sectioned with a razor blade and pressed onto nitrocellulose for 30 sec. The blot was blocked with 5% nonfat dry milk in 10 mM sodium phosphate, pH 7.2, 140 mM NaCl, 0.05% Tween-20, 0.05% NaN3 (PBST)for 2 hr at 37° C. The blot was probed with mouse monoclonal anti-HBsAg (Zymed Laboratories) at 1:1000 dilution in 2% nonfat dry milk in PBST for 2 hr at 23° C., before washing and detection with goat anti-mouse IgG-alkaline phosphatase conjugate (BioRad) and development with NBT and BCIP according to manufacturer's instructions (Genius 2 Kit, Boehringer-Mannheim).

Figure 11:
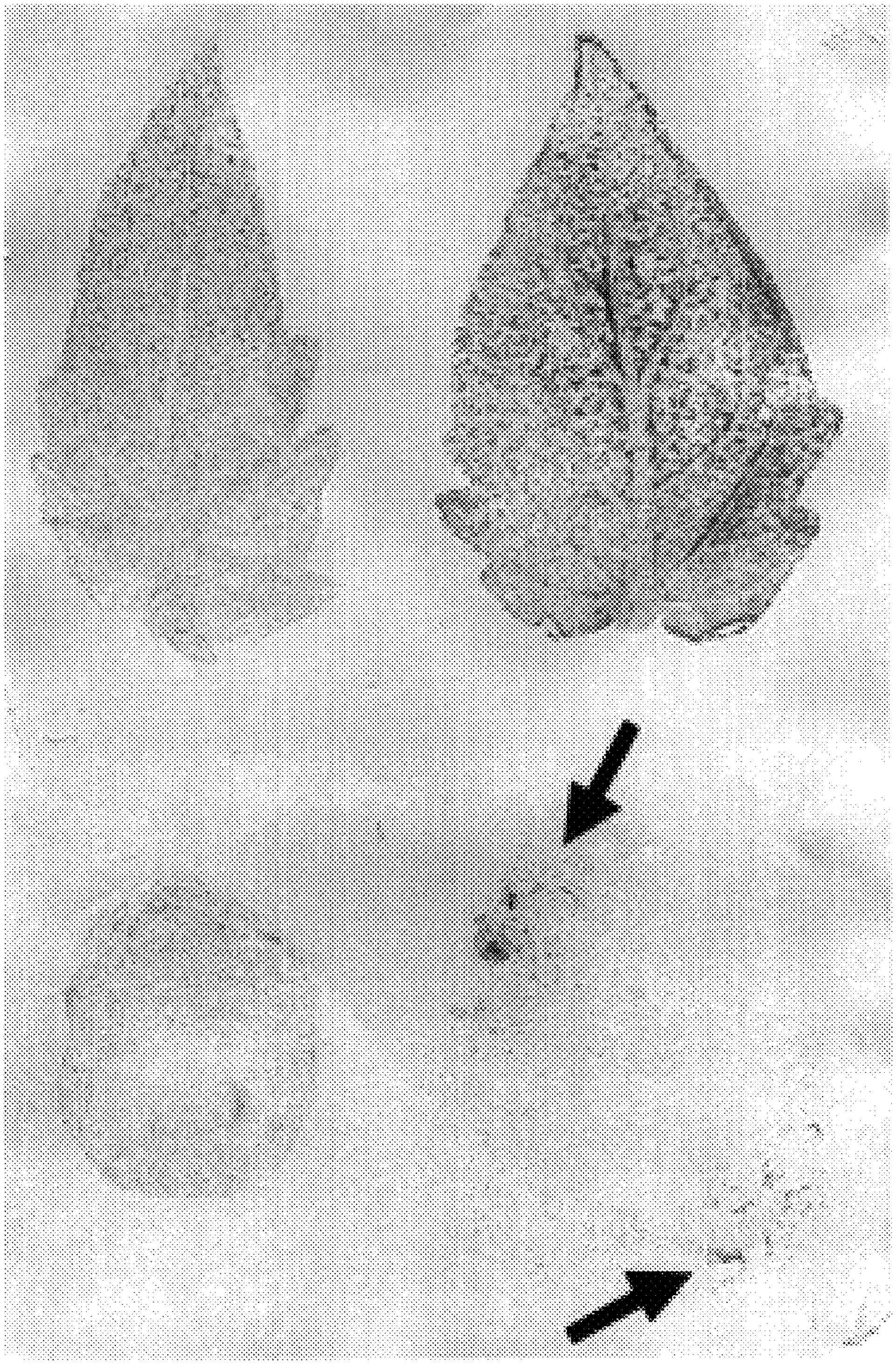
FIG. 11 is a tissue blot of tomato leaves.

Tissue blots on nitrocellulose, probed with monoclonal anti-HBsAg, as seen in FIG. 11, graphically demonstrate the presence of HBsAg in the transformed tomato tissues. Because this antibody does not react with SDS-denatured HBsAg, it was not possible to detect HBsAg on western blots of SDS-PAGE fractionated leaf proteins. FIG. 11 shows a tissue blot of transformed and untransformed tomato leaf and transformed tomato fruit. The faint color of the untransformed leaf blot on the left is from chlorophyll; very little purple staining was observed. The transformed leaf on the right and the transformed fruit at bottom showed purple precipitate indicating specific binding of the anti-HBsAg antibody.

EXAMPLE IV

A. Construction of Transmissible Gastroenteritis Virus Plasmid Expression Vector The Transmissible Gastroenteritis Virus (TEGV) coding sequence TGEV S-protein as described in Sanchez et al., 1992[75] was obtained from Dr. Lisa Welter (Ambico-West, Los Angeles, Calif.) as a PCR product cloned into plasmid pGEM-T (Promega Corp., Madison, Wis.). The 5' end was truncated six base pairs (6 bp) upstream of the translation initiation site by digestion with HincII. The 1.2 kilobase (kb) HincII/XhoI fragment was isolated and ligated into plasmid pBluescript KS (Stratagene, La Jolla, Calif.) which was previously digested with SmaI and XhoI. The resulting plasmid, pTG5', was then digested with BamHI and XhoI and the 1.2 kilobase (kb) fragment isolated. The 3.3 kilobase (kb) XhoI/SstI fragment, representing the 3' end of the S-protein coding region, was isolated and ligated together with the 1.2 kilobase (kb) BamHI/XhoI fragment from plasmid pTG5', representing the 5' end of the S-protein coding region, into plasmid pbluescript KS that had been digested with BamHI and SstI. The resulting plasmid, pKS-TG, was then digested with BamHI and SstI to give the entire 4.5 kilobase (kb) S-protein coding sequence, which was then ligated into the potato tuber expression vector plasmid pPS20[76] that was digested with BamHI and SstI and isolated from the GUS coding region. Plasmid pPS20 is a derivative of pBI101[77], and contains a kanamycin resistance cassette for selection of transformed plants. The resulting plasmid, pPS-TG, contains the S-protein coding region downstream of the patatin promoter, which drives tuber-specific expression in potato plants, and followed by the nopaline synthase polyadenylation signal.

B. Potato Transformation

*Agrobacterium tumefaciens* LBA4404 was transformed with plasmid pPS-TG by the freeze-thaw method of An[78], and the plasmid structure verified by restriction digestion. The Agrobacterium strain harboring plasmid pPS-TG was used for transformation of the potato variety "Atlantic." The potato transformation protocol was as described in Wenzler[79] and shoots were regenerated on media containing fifty milligrams per liter (50 mg/L) kanamnycin. Microtubers were induced on nodal stem segments as described by Wenzler.[79]

C. Analysis of S-protein Expression in Microtubers

Total RNA was extracted from microtubers using the method of Mason and Mullet[80], except that the microtubers were homogenized in three volumes of buffer in microcentrifuge tubes with pellet pestles, rather than grinding with liquid nitrogen ($N_2$). The RNA samples were assayed for S-protein mRNA by RNA dot blotting[81] and hybridization with a digoxygenin-labeled probe made by random-primed DNA synthesis (Genius 2 Kit, Boehringer-Mannheim, Indianapolis, Ind.). The 2.2 kilobase (kb) XhoI/XbaI fragment from the coding region of the TGEV S-protein gene was the template for probe synthesis. Hybridization and detection were done as per kit instructions (Genius 2 Kit, Boehringer-Mannheim, Indianapolis, Ind.), except that the hybridization buffer contained twenty-five hundredths molar (0.25 M) sodium phosphate, pH 7.0, five percent (5%) sodium lauryl sulfate, and ten millimolar ethylenediaminetetraacetic acid (10 mM EDTA). The results were only qualitative, but indicate that there was a range of different levels of expression of S-protein mRNA among the independent transformants, as is expected for a random insertion of the foreign gene into the host plant genome.

REFERENCES

The following references are specifically incorporated herein by reference in pertinent part for the reasons cited in the text.

1. Melnick, J. L., *Bul. W. H. O.* 67(2),105–112(1989).
2. Valenzuela, P. et al., *Nature* 298, 347–350(1982).
3. Kupper, H. et al, *Nature* 289, 555–559(1981).
4. Benfey, P. N. and Chua, N. H., *Science* 244, 174–181 (1989).
5. Shah, D. M. et al., U.S. Pat. No. 4,940,835 (1990).
6. Horsch, R. B. et al. in *Plant Molecular Biology Manual* A5, Kluwer Academic Publishers, Dordrecht (1988) p. 1–9.
7. Rhodes, C. A. et al., *Science* 240, 204–207 (1989).
8. Toriyama, K. et al., *Bio/Technology* 6, 1072–1074 (1988).
9. Zhang, W. & Wu, R., *Theor. Appl. Genet.* 76, 835–840 (1988).
10. Wu, R. in *Plant Biotechnology,* Kung, S. and Arntzen, C. J., eds., Butterworth Publishers, Boston, Mass. (1989) p. 35–51.
11. *Vaccination Strategies of Tropical Diseases,* ed., Liew, F. W., CRC Press, Boca Raton, Fla.; (1989).
12. *New Strategies in Parasitology,* ed., McAdam, K. P. W. J., Churchill Livingstone, New York, N.Y.; (1989).
13. Murray, P. K., Vaccine 7, 291–299 (1989).
14. Weber, J. L. et al., *Exp. Parasitology* 63, 295–300 (1987).
15. Hoffman, S. L. et al., *Science* 252, 520–521 (1991).
16. Khusmith, S. et al., *Science* 252, 715–718 (1991).
17. Kaslow, D. C. et al., *Science* 252, 1310–1313 (1991).
18. Frasch, A. C. C. et al., *Parasitology Today* 7, 148–151 (1991).
19. Mitchell, G. F. et al., *Parasitology Today* 5, 34–37 (1989).
20. Capron, A. et al., *Science* 238 1065–1072 (1987).
21. Lanar, D. et al., *Science* 234, 593–596 (1986).
22. Deak, M. et al., *Plant Cell Rep.* 5, 97–100 (1986).
23. McCormick S. et al., *Plant Cell Rep* 5, 81–84 (1986).
24. Shahin, E. and Simpson, R., *Hort.Sci.* 21, 1199–1201 (1986).
25. Umbeck, P. et al., *Bio/Technology* 5, 263–266 (1987).
26. Christou, P. et al., *Trends Biotechnol.* 8, 145–151 (1990).
27. Datta, S. K. et al., *Bio/Technology* 8, 736–740 (1990).
29. Hinchee, M. A. W. et al., *Bio/Technology* 6, 915–922 (1988).
30. Raineri, D. M. et al., *Bio/Technology* 8, 33–38 (1990).
31. Fromm, M. E. et al., *Bio/Technology* 8, 833–839 (1990).
32. Gordon-Kamm, W. J. et al., *The Plant Cell* 2, 603–618 (1990).
33. Potrykus, I., *Annu. Rev. Plant Physiol., Plant Mol. Biol.* 42, 205–225 (1991).
34. Shimamoto, K., et al., *Nature* 338, 274–276 (1989).
35. Klee, H. et al., *Annu. Rev. Plant Physiol.* 38, 467–486 (1987).
36. Klee, H. J. and Rogers, S. G. in *Cell Culture and Somatic Cell Genetics of Plants,* Vol. 6, *Molecular Biology of Plant Nuclear Genes,* eds. Schell, J., and Vasil, L. K., Academic Publishers, San Diego, Calif. (1989) p. 2–25.
37. Gatenby, A. A. in *Plant Biotechnology,* eds. Kung, S. and Arntzen, C. J., Butterworth Publishers, Boston, Mass. (1989) p. 93–112.
38. Paszkowski, J., et al. in *Cell Culture and Somatic Cell Genetics of Plants,* Vol. 6, *Molecular Biology of Plant Nuclear Genes* eds. Schell, J., and Vasil, L. K., Academic Publishers, San Diego, Calif. (1989) p. 52–68.
39. Klein, T. M., et al. in *Progress in Plant Cellular and Molecular Biology,* eds. Nijkamp, H. J. J., Van der Plas, J. H. W., and Van Aartrijk, J., Kluwer Academic Publishers, Dordrecht, (1988) p. 56–66.
40. DeWet, J. M. J., et al. in *Experimental Manipulation of Ovule Tissue,* eds. Chapman, G. P. and Mantell, S. H. and Daniels, W. Longman, London, (1985) p. 197–209.
41. Zhang, H. M. et al., *Plant Cell Rep.* 7, 379–384 (1988).
42. Fromm, M. E. et al., *Nature* 319, 791–793 (1986).
43. Hess, D. *Int. Rev. Cytol.* 107, 367–395 (1987).
44. Klein, T. M. et al., *Bio/Technology* 6, 559–563 (1988).
45. McCabe, D. E. et al., *Bio/Technology* 6, 923–926 (1988).
46. Sanford, J. C., *Physiol. Plant.* 79, 206–209 (1990).
47. Neuhaus G. et al., *Theor. Appl. Genet.* 75, 30–36 (1987).
48. Neuhaus, G. and Spangenberg, G., *Physiol. Plant.* 79, 213–217 (1990).
49. Ohta, Y.. *Proc. Natl. Acad. Sci. USA* 83, 715–719 (1986).
51. Futterer, J., et al., *Physiol. Plant.* 79, 154–157 (1990).
52. Watson, J. D. et al, *Recombinant DNA, a Short Course,* Scientific American Books, dist. W. H. Freeman & Co., New York, N.Y. (1983) p. 164–175.
53. White, F. F. in *Plant Biotechnology,* eds. Kung, S. and Arntzen, C. J., Butterworth Publishers, Boston, Mass. (1989) p. 3–34.
54. Fraley, R. T. in *Plant Biotechnology,* eds. Kung, S. and Arntzen, C. J., Butterworth Publishers, Boston, Mass. (1989), p. 395–407.
55. Elliston, K. and Messing, J. in *Plant Biotechnology,* eds. Kung, S. and Arntzen, C. J., Butterworth Publishers, Boston, Mass. (1989), p. 115–139.
56. Wenzler, H. C. et al., *Plant Mol. Biol.* 12, 41–45 (1989).
57. Weising, K. et al., *Annu. Rev. Genet.* 22, 421–477 (1988).
58. An, G., *Meth. Enzymol.* 153, 292–305 (1987).
59. Maniatis, T., et al., *Molecular Cloning, A Laboratory Manual,* Cold Spring Harbor Laboratory, Cold Spring Harbor, N.Y. (1982), p. 368–369.
60. Chang, A. et al., *Proc. Natl. Acad. Sci., U.S.A.* 86, 9611 (1989).
61. Peng, Y. W. and Lam, D. M. K., *Vis. Neurosci.* 6, 357 (1991).
62. Pershing, D. H. et al., *Proc. Natl. Acad. Sci. U.S.A.* 82, 3440 (1985).
64. Pasek, M. and Goto, T., *Nature* 282, 575–579 (1979).
65. Cattaneo, R., *Nature* 305, 336–338 (1983).
66. Jefferson, R. et al., *EMBO J.* 6, 3901–3907 (1987).
67. Carrington, J. et al., *Plant Cell* 3, 953–962 (1991).
68. Mason, H. et al., *Plant Molecular Biology* 11, 845–856 (1988).

69. Ganem, D. and Varmus, H., *Ann. Rev. Biochem.* 56, 651–693 (1987).
70. Gerilin, H. et al., *J. Virol.* 7, 569–576 (1971).
71. Tiollais, P. et al., *Science* 213, 406–411 (1981).
72. Mason H. S., et al., *Proc. Natl. Acad. Sci. USA,* 89, 11745–11749 (1992).
73. Carrington, J. et al., *J. Virol.* 64, 1590–1597 (1990).
74. Bradford, M. M., *Anal. Biochem.* 72, 248–254 (1976).
75. Sanchez, C. M., et al., *Virology* 190, 92–115 (1992).
76. Wenzler, H. C., et al., *Plant Mol. Biol.* 12, 41–50 (1989).
77. Jefferson, R. A., et al., *EMBO J.* 13, 3901–3907 (1987).
78. An, G., *Meth. Enzymol.* 153, 292–305 (1987).
79. Wenzler, H. C., et al., *Plant Science* 63, 79–85 (1989).
80. Mason, H. S. et al., *Plant Cell* 2, 569–579 (1990).
81. Sambrook, J., et al., *Molecular Cloning: A Laboratory Manual,* 2nd Edition, Cold Spring Harbor Laboratory Press.

The foregoing description of the invention has been directed to a particular preferred embodiments in accordance with the requirements of the patent and statutes and for purposes of explanation and illustration. It will become apparent to those skilled in the art that modifications and changes may be made without departing from the scope and the spirit of the invention.

What is claimed is:

1. An orally acceptable immunogenic composition comprising unpurified or partially purified recombinant viral immunogen expressed in a plant, wherein said immunogen is expressed in the plant at a level such that upon oral administration of said composition to an animal, an immunogenic response is observed.

2. The vaccine of claim 1 wherein said immunogen is capable of generating an immunogenic response when the immunogen interacts with a mucosal membrane.

3. The vaccine of claim 1 wherein the immunogen is capable of binding a glycosylated molecule on the surface of a membrane of a mucosal cell.

4. The vaccine of claim 1 wherein said immunogen is a chimeric protein.

5. The vaccine of claim 1 wherein said immunogen is an immunogen derived from a hepatitis virus.

6. An orally acceptable immunogenic composition comprising unpurified or partially purified recombinant viral immunogen expressed in a plant, wherein said immunogen is expressed in the plant at a level such that upon oral administration of said composition to an animal, an immunogenic response is observed, said viral immunogen being an immunogenic protein from a virus selected from the group consisting of transmissible gastroenteritis virus and hepatitis virus.

7. A vaccine comprising a immunogen of hepatitis virus expressed in a plant, wherein said immunogen is capable of binding a glycosylated molecule on a surface of a membrane mucosal cell.

8. A plant composition comprising a viral antigen which triggers production of antibodies and which is derived from a hepatitis B virus surface antigen or transmissible gastroenteritis virus spike protein, and plant material; said antigen being a product produced by the method of expressing said immunogen in a transgenic plant, said plant material being in a form chosen from the group consisting of a whole plant, plant part, or a crude plant extract.

9. An anti-hepatitis B vaccine comprising the composition of claim 8 wherein said antigen is derived from hepatitis B virus surface antigen.

10. An anti-transmissible gastroenteritis vaccine comprising the composition of claim 8 wherein said antigen is derived from transmissible gastroenteritis virus spike protein.

* * * * *